(12) United States Patent
Pape et al.

(10) Patent No.: US 6,959,214 B2
(45) Date of Patent: Oct. 25, 2005

(54) IMPLANTABLE MEDICAL DEVICE FOR MEASURING MECHANICAL HEART FUNCTION

(75) Inventors: Forrest C. M. Pape, New Brighton, MN (US); Paul J. Huelskamp, St. Paul, MN (US)

(73) Assignee: Medtronic, Inc., Minneapolis, MN (US)

(*) Notice: Subject to any disclaimer, the term of this patent is extended or adjusted under 35 U.S.C. 154(b) by 655 days.

(21) Appl. No.: 09/996,138

(22) Filed: Nov. 28, 2001

(65) Prior Publication Data

US 2003/0100925 A1 May 29, 2003

(51) Int. Cl.[7] ............................................. A61N 1/362
(52) U.S. Cl. ....................................................... 607/17
(58) Field of Search ...................... 607/6, 9, 14, 17–19, 607/23–25, 119, 121, 123; 600/508, 485, 488, 510, 518, 526, 527

(56) References Cited

U.S. PATENT DOCUMENTS

| | | | |
|---|---|---|---|
| 3,937,226 A | 2/1976 | Funke | 128/419 |
| 3,949,758 A | * 4/1976 | Jirak | 607/28 |
| 4,030,508 A | 6/1977 | Thalen | 128/418 |

(Continued)

OTHER PUBLICATIONS

Cazeau et al., Four Chamber Pacing in Dilated Cardiomyopathy, PACE, vol. 17, Nov. 1994 Part II, pp 1974–1979.

Daubert et al., Permanent Left Ventricular Pacing with Transvenous Leads Inserted Into the Coronary Veins, PACE, vol. 21, Jan. 1998 Part II, pp 239–245.

Daubert et al., Permanent Dual Atrium Pacing in Major Interatrial Conduction Blocks: A Four Year Experience, PACE, vol. 16, Apr. 1993 Part II, p 885.

Durrer et al., Total Excitation of the Isolated Human Heart, Circulation, vol. XLI, Jun. 1970, pp. 899–912.

Daubert et al., Renewal of Permanent Left Atrial Pacing Via the Coronary Sinus, PACE, vol. 15 Part II, Apr. 1992, p 572.

Weston, et al., A Prototype Coronary Electrode Catheter for Intracoronary Electrogram Recording, The American Journal of Cardiology, vol. 70, Dec. 1, 1992, pp 1492–1493.

Hopps et al., Electrical Treatment of Cardiac Arrest: A Cardiac Stimulator–Defibrillator in Surgery, vol. 36, No. 4, pp 833–849.

*Primary Examiner*—Jeffrey R. Jastrzab
(74) *Attorney, Agent, or Firm*—Michael C. Soldner; Girma Wolde-Michael

(57) ABSTRACT

An implantable device for measuring mechanical heart function of selected heart chambers using a heart contraction detection system that includes a magnetic field sensor. The system may be used for monitoring signs of acute or chronic cardiac heart failure, to enable diagnosis of the condition of the heart, to prescribe appropriate therapies, and to assess delivered pacing therapies. Distance measurements within the heart are made using the magnetic field sensor which is implanted at a sensor site in or on one of the right or left ventricle. A magnet implanted at a site relative to the other of the left or right heart ventricle is sufficiently spaced at a distance that fluctuates with expansion and contraction of the ventricles. The magnetic field sensor provides a sensor output signal having a signal magnitude proportional to the magnetic field strength of the magnet, and which is indicative of changing cardiac dimensions.

7 Claims, 8 Drawing Sheets

U.S. PATENT DOCUMENTS

| | | | |
|---|---|---|---|
| 4,088,140 A | | 5/1978 | Rockland et al. ............ 128/419 |
| 4,237,900 A | * | 12/1980 | Schulman et al. ........... 600/301 |
| 4,332,259 A | | 6/1982 | McCorkle, Jr. ............... 128/786 |
| 4,354,497 A | | 10/1982 | Kahn ........................... 128/419 |
| 4,458,677 A | | 7/1984 | McCorkle, Jr. ............... 128/786 |
| 4,493,325 A | * | 1/1985 | Hartlaub et al. ............... 607/14 |
| 4,674,518 A | | 6/1987 | Salo ............................ 128/695 |
| 4,730,619 A | | 3/1988 | Koning et al. ................ 128/419 |
| 4,813,435 A | * | 3/1989 | Arms ............................ 600/587 |
| 4,928,688 A | | 5/1990 | Mower ......................... 128/419 |
| 5,129,394 A | * | 7/1992 | Mehra ........................... 607/23 |
| 5,161,540 A | * | 11/1992 | Mueller ........................ 600/508 |
| 5,174,289 A | | 12/1992 | Cohen ......................... 128/419 |
| 5,243,976 A | | 9/1993 | Ferek-Petric et al. ........... 607/6 |
| 5,267,560 A | | 12/1993 | Cohen ........................... 607/25 |
| 5,403,356 A | | 4/1995 | Hill et al. ...................... 607/14 |
| 5,417,717 A | | 5/1995 | Salo et al. ..................... 607/18 |
| 5,431,691 A | * | 7/1995 | Snell et al. .................... 607/27 |
| 5,458,621 A | * | 10/1995 | White et al. .................... 607/5 |
| 5,514,161 A | | 5/1996 | Limousin ........................ 607/9 |
| 5,549,650 A | * | 8/1996 | Bornzin et al. ................ 607/24 |
| 5,564,434 A | | 10/1996 | Halperin et al. ............. 128/748 |
| 5,584,867 A | | 12/1996 | Limousin et al. ............... 607/9 |
| 5,626,623 A | | 5/1997 | Kieval et al. .................. 607/23 |
| 5,628,777 A | * | 5/1997 | Moberg et al. ............... 607/122 |
| 5,674,259 A | | 10/1997 | Gray ............................ 607/20 |
| 5,720,768 A | | 2/1998 | Verboven-Nelissen .......... 607/9 |
| 5,730,141 A | * | 3/1998 | Fain et al. ................... 600/518 |
| 5,792,203 A | | 8/1998 | Schroeppel ................... 607/30 |
| 5,797,970 A | | 8/1998 | Pouvreau ....................... 607/9 |
| 5,902,324 A | | 5/1999 | Thompson et al. ............. 607/9 |
| 6,104,949 A | | 8/2000 | Pitts Crick et al. ......... 600/547 |
| 6,129,744 A | | 10/2000 | Boute ........................... 607/25 |
| 6,219,579 B1 | | 4/2001 | Bakels et al. ................. 607/17 |
| 6,277,078 B1 | * | 8/2001 | Porat et al. .................. 600/486 |
| 6,421,565 B1 | * | 7/2002 | Hemmingsson .............. 607/17 |

\* cited by examiner

IMPLANTABLE MEDICAL DEVICE FOR MEASURING MECHANICAL HEART FUNCTION

FIELD OF THE INVENTION

The present invention relates generally to implantable medical devices (IMDs) for measuring mechanical heart function of selected heart chambers using a magnetic field sensor based, heart contraction detection and measuring system.

BACKGROUND OF THE INVENTION

Patients suffering from chronic CHF manifest an elevation of left ventricular end-diastolic pressure, according to the well-known heterometric autoregulation principles espoused by Frank and Starling. This may occur while left ventricular end-diastolic volume remains normal due to a decrease in left ventricular compliance concomitant with increased ventricular wall stiffness. CHF due to chronic hypertension, ischemia, infarct or idiopathic cardiomyopathy is associated with compromised systolic and diastolic function involving decreased atrial and ventricular muscle compliance. These may be conditions associated with chronic disease processes or complications from cardiac surgery with or without specific disease processes. Most heart failure patients do not normally suffer from a defect in the conduction system leading to ventricular bradycardia, but rather suffer from symptoms which may include a general weakening of the contractile function of the cardiac muscle, attendant enlargement thereof, impaired myocardial relaxation and depressed ventricular filling characteristics in the diastolic phase following contraction. Pulmonary edema, shortness of breath, and disruption in systemic blood pressure are associated with acute exacerbations of heart failure.

All these disease processes lead to insufficient cardiac output to sustain mild or moderate levels of exercise and proper function of other body organs, and progressive worsening eventually results in cardiogenic shock, arrhythmias, electromechanical dissociation, and death. In order to monitor the progression of the disease and to assess efficacy of prescribed treatment, it is necessary to obtain accurate measures of the heart geometry, the degree of heart enlargement, and the mechanical pumping capability of the heart, e.g., ejection fraction, under a variety of metabolic conditions the patient is likely to encounter on a daily basis. These parameters are typically measured through the use of external echocardiogram equipment in the clinical setting. However, the measurement procedure is time consuming to perform for even a resting patient and cannot be practically performed replicating a range of metabolic conditions. Typically, the echocardiography procedure is performed infrequently and months or years may lapse between successive tests, resulting in a poor understanding of the progress of the disease or whether or not intervening drug therapies have been efficacious. Quite often, only anecdotal evidence from the patient is available to gauge the efficacy of the prescribed treatment.

Moreover, in many cases, diseased hearts exhibiting LVD and CHF also have conduction defects wherein cardiac depolarizations that naturally occur in one upper or lower heart chamber are not always conducted in a timely fashion either within the heart chamber or to the other upper or lower heart chamber. In such cases, the right and left heart chambers do not contract in optimum synchrony with each other, and cardiac output suffers due to the conduction defects. In addition, spontaneous depolarizations of the left atrium or left ventricle occur at ectopic foci in these left heart chambers, and the natural activation sequence is grossly disturbed. The natural electrical activation system through the heart involves sequential events starting with the sinoatrial (SA) node, and continuing through the atrial conduction pathways of Bachmann's bundle and internodal tracts at the atrial level, followed by the atrio-ventricular (AV) node, Common Bundle of His, right and left bundle branches, and final distribution to the distal myocardial terminals via the Purkinje fiber network. A common type of intra-atrial conduction defect is known as intra-atrial block (IAB), a condition where the atrial activation is delayed in getting from the right atrium to the left atrium. In left bundle branch block (LBBB) and right bundle branch block (RBBB), the activation signals are not conducted in a normal fashion along the right or left bundle branches respectively. Thus, in a patient with LBBB or RBBB, the activation of the ventricles is slowed, and the QRS is seen to widen due to the increased time for the activation to traverse the conduction path. For example, in a patient with LBBB, the delay in the excitation from the RV to the LV can be as high as 120 to 150 ms. Cardiac output deteriorates because the contractions of the right and left heart chambers are not synchronized sufficiently to eject the maximal blood volume. Furthermore, significant conduction disturbances between the right and left atria can result in left atrial flutter or fibrillation.

More particularly, as described in commonly assigned U.S. Pat. No. 6,129,744, patients suffering from LVD are also known to have elevated levels of catecholamines at rest because the body is attempting to increase cardiac output that induce a higher resting heart rate. In addition, the QT interval for such a patient is affected by the catecholamine level and thus has a changed pattern during exercise as well. These patients have a decreased QT response, or smaller change in QT, during exercise, such that the QT interval shortening during exercise is smaller than that found normally. Although QT interval is influenced independently by heart rate alone, as well as by exercise and catecholemines, it is not known to what extent each of these factors or both are responsible for the changed QT response to exercise in LVD patients. However, it is known that patients suffering LVD clearly have a different pattern of QT interval shortening during exercise. Moreover, the changed conductive patterns or a heart in heart failure are manifested by other changes in the PQRST waveforms, particularly an abnormally wide or long duration of the ventricular depolarization signal, or QRS.

These observed conduction defects have caused physicians to prescribe implantation of conventional, atrioventricular (AV) synchronous pacing systems, including DDD and DDDR pacing systems, marketed by Medtronic, Inc. and other companies, in certain patients for treatment of heart failure symptoms. Certain patient groups suffering heart failure symptoms with or without bradycardia tend to do much better hemodynamically with AV synchronous pacing due to the added contribution of atrial contraction to ventricular filling and subsequent contraction. However, fixed or physiologic sensor driven rate responsive pacing in such patients does not always lead to improvement in cardiac output and alleviation of the symptoms attendant to such disease processes because it is difficult to assess the degree of compromise of cardiac output caused by CHF and to determine the pacing parameters that are optimal for maximizing cardiac output, particularly the AV delay.

Determining an optimal AV delay requires performing echocardiography studies or obtaining pressure data involving an extensive patient work-up as set forth in commonly assigned U.S. Pat. No. 5,626,623. Moreover, conventional DDD and DDDR pacemakers pace and sense only in the right atrium and right ventricle and cannot alleviate or alter IAB, LBBB, RBBB and QT interval widening.

Consequently, while some improvement has been reported in certain patients receiving two-chamber DDD or DDDR AV sequential pacemakers, the efficacy of the treatment is not established for larger patient populations. A number of proposals have been advanced for providing pacing therapies to alleviate heart failure conditions and restore synchronous depolarization and contraction of a single heart chamber or right and left, upper and lower, heart chambers as described in detail in the above referenced '744 patent and in commonly assigned U.S. Pat. Nos. 5,403,356, 5,797,970 and 5,902,324 and in U.S. Pat. Nos. 5,720,768 and 5,792,203. The proposals appearing in U.S. Pat. Nos. 3,937,226, 4,088,140, 4,548,203, 4,458,677, 4,332,259 are summarized in U.S. Pat. Nos. 4,928,688 and 5,674,259. The advantages of providing sensing at pace/sense electrodes located in both the right and left heart chambers is addressed in the '688 and '259 patents, as well as in U.S. Pat. Nos. 4,354,497, 5,174,289, 5,267,560, 5,514,161, and 5,584,867.

The medical literature also discloses a number of approaches of providing bi-atrial and/or bi-ventricular pacing as set forth in: Daubert et al., "Permanent Dual Atrium Pacing in Major Intra-atrial Conduction Blocks: A Four Years Experience", *PACE* (Vol. 16, Part II, NASPE Abstract 141, p.885, April 1993); Daubert et al., "Permanent Left Ventricular Pacing With Transvenous Leads Inserted Into The Coronary Veins", *PACE* (Vol. 21, Part II, pp. 239–245, January 1998); Cazeau et al., "Four Chamber Pacing in Dilated Cardiomyopathy", *PACE* (Vol. 17, Part II, pp. 1974–1979, November 1994); and Daubert et al., "Renewal of Permanent Left Atrial Pacing via the Coronary Sinus", *PACE* (Vol. 15, Part II, NASPE Abstract 255, p. 572, April 1992).

In most cases, it has been proposed that bi-ventricular pacing pulses be applied simultaneously to the right and left ventricles. An observation is made in commonly assigned U.S. Pat. No. 6,219,579 that the exact timing of mechanical events are important for properly controlling right and left heart chamber pacing so as to optimize left ventricular output. Specifically, it is known that actual contraction of one ventricular chamber before the other has the effect of moving the septum so as to impair full contraction in the later activated chamber. Thus, while concurrent or simultaneous pacing of the left and right ventricle may achieve a significant improvement for CHF patients, it is better to provide for pacing of the two ventricles in such a manner that the actual mechanical contraction of the left ventricle, with the consequent closing of the valve, occurs in a desired time relationship with respect to the mechanical contraction of the right ventricle and closing of the right value. For example, if conduction paths in the left ventricle are impaired, delivering a pacing stimulus to the left ventricle at precisely the same time as to the right ventricle may nonetheless result in left ventricular contraction being slightly delayed with respect to the right ventricular contraction.

In the above-referenced '324 patent, an AV synchronous pacing system is disclosed providing three or four heart chamber pacing through pace/sense electrodes located in or adjacent one or both of the right and left atrial heart chambers and in or adjacent to the right and left ventricular heart chambers. During an AV delay and during a V-A escape interval, a non-refractory ventricular sense event detected at either the right or left ventricular pace/sense electrodes starts a programmable conduction delay window (CDW) timer. A ventricular pace pulse is delivered to the other of the left or right ventricular pace/sense electrodes at the time-out of the CDW if a ventricular sense event is not detected at that site while the CDW times out. However, it is not always easy to determine just how to program the CDW duration to optimize the hemodynamics of the heart. As a consequence, it is important to provide a technique for measurement of mechanical events, such as a mechanical closure point of each of the ventricles, so as to be able to accurately program the sequence of pacing to achieve the desired dual ventricular pacing which optimizes ejection fraction, or cardiac output, for the individual patient.

Moreover, while such AV sequential, three or four-chamber pacing systems can be programmed to at least initially restore right and left and upper and lower heart synchrony in the clinical setting, they are not always able to maintain that synchrony over a range of heart rates and as the patient is exposed to other conditions of daily life including stress and exercise. Therefore, a number of other approaches have been proposed and advanced involving implantation of physiologic cardiac monitors for deriving and storing electrical EGM signals and mechanical performance indicating parameters over a prolonged time period and development of three and four-chamber pacing systems having the same capabilities. For example, the Medtronic® CHRONICLE® IHM implantable heart monitor senses blood pressure within a heart chamber and the EGM of the heart using an EGM and pressure sensing lead of the type disclosed in commonly assigned U.S. Pat. No. 5,564,434. Such implantable monitors when implanted in patients suffering from cardiac arrhythmias or heart failure accumulate date and time stamped data that can be of use in determining the condition of the heart over an extended period of time and while the patient is engaged in daily activities.

It is understood that the amount of blood being pumped by the heart is governed not only by the intrinsic or multi-chamber paced heart rate, but also by the stroke volume of the heart, which is adversely lessened by heart failure. It has been recognized that it would be desirable to measure the contractility or displacement of the heart wall to determine the hemodynamic efficiency of the heart alone in an implanted monitor or in the context of controlling the operations of therapy delivery IMDs.

For example the use an accelerometer positioned within a lead that is located within one of the chambers of the heart is disclosed in U.S. Pat. No. 5,549,650. The lead is attached to one of the walls of the heart so that movement of the wall of the heart causes the accelerometer that to develop an accelerometer signal that is processed to provide a first signal indicative of the contractility of the heart and a second signal indicative of the physical displacement of the wall of the heart. It is proposed in U.S. Pat. No. 4,730,619 to derive a measure of the ejection time of the ventricles, which is derived from the duration of contraction of the right ventricle, which is determined from changes in right ventricular pressure. The right ventricular blood pressure is measured by a hermetically sealed absolute strain gauge transducer or a piezoresistive transducer mounted within a transvenous lead. The signals derived in the '650 and '619 patent are employed by the pacing system to adjust the pacing parameters to improve the hemodynamic efficiency of the heart as this information is directly related to the volume of blood being pumped by the heart during each ventricular contraction.

In an approach related to monitoring rejection of heart transplants, a magnetic field responsive Hall effect device and a permanent magnet are implanted directly across the septum or a heart wall as taught in U.S. Pat. No. 5,161,540, and the Hall effect device is powered by an implantable generator and telemetry transceiver. The compliance of the heart wall is monitored to detect any loss of compliance characteristic of rejection of the heart transplant is transmitted from the implanted system.

A discussion of a wide number of mechanical and electrical parameter sensors employed in the art to assess cardiac functions and hemodynamic efficiency is set forth in U.S. Pat. No. 5,243,976. In the '976 patent, continuous wave (CW) and pulsed wave (PW) Doppler emitters are incorporated into pacing leads to measure blood flow, and the flow measurements are employed to regulate atrial and ventricular pacing parameters and for other purposes.

In the above-referenced '579 patent, impedance measurements are made in or across the heart chambers from which accurate timing signals are obtained reflecting mechanical actions, e.g., valve closures, so that accurate timing information is available for controlling electrical activation and resultant mechanical responses for the respective different heart chambers. The impedance or mechanical sensing determinations are preferably made by multiplexing through fast switching networks to obtain the desired impedance measurements in different heart chambers. In a preferred embodiment, control of left heart pacing, is based primarily upon initial detection of a spontaneous signal in the right atrium, and upon sensing of mechanical contraction of the right and left ventricles. In a heart with normal right heart function, the right mechanical AV delay is monitored to provide the timing between the initial sensing of right atrial activation (P-wave) and right ventricular mechanical contraction. The left heart is controlled to provide pacing which results in left ventricular mechanical contraction in a desired time relation to the right mechanical contraction; e.g., either simultaneous or just preceding the right mechanical contraction; cardiac output is monitored through impedance measurements, and left ventricular pacing is timed to maximize cardiac output. In patients with IAB, the left atrium is paced in advance of spontaneous depolarization, and the left AV delay is adjusted so that the mechanical contractions of the left ventricle are timed for optimized cardiac output from the left ventricle.

A CHF monitor/stimulator is disclosed in commonly assigned U.S. Pat. No. 6,104,949 that senses the trans-thoracic impedance as well as patient posture and provides a record of same to diagnose and assess the degree and progression of CHF. The sensed trans-thoracic impedance is dependent on the blood or fluid content of the lungs and assists in the detection and quantification of pulmonary edema symptomatic of CHF. Trans-thoracic impedance is affected by posture, i.e. whether the subject is lying down or standing up, and the sensed trans-thoracic impedance is correlated to the output of the patient posture detector to make a determination of presence of and the degree of pulmonary edema for therapy delivery and/or physiologic data storage decisions.

A monitor/stimulator is disclosed in U.S. Pat. No. 5,417,717 that monitors and assesses level of cardiac function then permits a physician to arbitrate the therapy mode, if therapy is indicated. The monitor stimulator assesses impedance, EGM, and/or pressure measurements, and then calculates various cardiac parameters. The results of these calculations determine the mode of therapy to be chosen. Therapy may be administered by the device itself or a control signal may be telemetry transmitted to various peripheral devices aimed at enhancing the heart's function. Alternatively, the device may be programmed to monitor and either store or telemeter information without delivering therapy.

Particularly, the implantable monitor/stimulator monitors conventional parameters of cardiac function and contractile state, including all phases of the cardiac cycle. Thus, assessments of contractile state measured include indices of both cardiac relaxation and contraction. Utilizing the dual source ventricular impedance plethysmography technique described in U.S. Pat. No. 4,674,518, the monitor/stimulator monitors cardiac function by assessing hemodynamic changes in ventricular filling and ejection or by calculating isovolumic phase indices by known algorithms. The primary calculations involve: (1) the time rate of change in pressure or volume, dP/dt or dV/dt, as isovolumic indicators of contractility; (2) ejection fraction as an ejection phase index of cardiac function according to the known quotient of stroke volume divided by end diastolic volume; (3) Maximal elastance, $E_M$; (4) regression slope through maximal pressure-volume points as a further ejection phase index of contractility using the method of Sagawa; (5) stroke work according to the known pressure-volume integration; (6) the time course of minimum (end) diastolic pressure-volume measurements according to the method of Glantz as a measure of diastolic function; and (7) cardiac output calculation according to the known product of heart rate and stroke volume as an index of level of global function.

While measurement and storage of this group of parameters of cardiac function and contractile state can provide valuable information about the state of heart failure, the sensors are not always easy to implant so that they perform reliably chronically and under the range of conditions encountered by the patient and resulting from progression of the heart failure.

The proposed systems employing locally disposed accelerometers at one or more location in the heart or distributed impedance measuring electrodes to detect and measure heart motion and to derive the above-described parameters are difficult to implement and subject to outside influences that distort the signals. The accelerometer signal needs to be filtered to reject output signals due to non-cardiac contraction forces transmitted through the body by exercise, respiration and blows to the body. The sensitive semiconductor or miniature beam elements of accelerometers are subject to damage or change in sensitivity over time. The foreign body reaction tissue build-up encasing the accelerometer structure can dampen its response to movement or inhibit its movement.

Implantable pressure sensors that employ a diaphragm that is deflected by contacting blood have proven to be problematic. The foreign body reaction induced tissue encapsulation occurring over the diaphragm can decrease its sensitivity to blood pressure fluctuations.

Impedance measuring electrodes on lead bodies in a heart chamber or cardiac blood vessel also become encased in tissue which may tend to change the impedance that is measured over time. Impedance across the right and left ventricles and interventricular septum is also influenced by breathing and patient activity such that these influences must also be filtered out of the signal.

Momentary changes to a patient's autonomic state can change blood pressure (P), heart rate, and pressure rate of change (dP/dt) contractility measures and not be reflective of a "true" functional state change of the heart. Such momentary changes in autonomic state are caused by postural changes as noted in the above-referenced '949 patent and other movements, such as bending down to pick up an object or suddenly standing up from a sitting or reclining position.

It would be desirable to obtain cardiac data that provides an enhanced assessment of cardiac function and heart failure state that are less sensitive to exercise, breathing, patient movements and posture changes, that is simple, inexpensive, easy to implant, reliable and not prone to loss of sensitivity or drift due to tissue encapsulation.

Given the demonstrated feasibility of four-chamber cardiac pacing, and the availability of techniques for sensing natural cardiac signals and mechanical events, there nonetheless remains a need for developing a system which is adapted to the cardiac condition of a patient with CHF, so as to provide pacing sequences which are tuned for improving cardiac output, and in particular for improving left heart function.

SUMMARY OF THE INVENTION

In view of the above need, the present invention provides a system and method for monitoring cardiac signals and the contraction and expansion of the heart chambers and processing such signals within an IMD to provide data related to the mechanical performance of the heart or the response of the heart to pacing therapies.

If the IMD provides a pacing function, the heart's response to the applied pacing regimen can be assessed from the magnitude, timing and duration of the distance measurements to assess mechanical performance. The distance measurements are stored in IMD memory for later uplink telemetry transmission to an external medical device or concurrently uplink telemetry transmitted to an external medical device. The accumulated data may reflect a trend that can be analyzed to assess the onset or progression of heart failure of the above-described types.

The system and method of the present invention can be advantageously employed in the detection of electromechanical dissociation during pacing or arrhythmias, differentiation of hemodynamically significant and insignificant ventricular tachycardias, monitoring of cardiac output, mechanical confirmation of capture or loss of capture for autocapture algorithms, optimization of multi-site pacing for heart failure, rate responsive pacing based on myocardial contractility, detection of syncope, detection or classification of atrial and ventricular tachyarrhythmias, automatic adjustment of sense amplifier sensitivity based on detection of mechanical events, determination of pacemaker mode switching, determining the need for fast and aggressive versus slower and less aggressive anti-tachyarrhythmia therapies, or determining the need to compensate for a weakly beating heart after therapy delivery, and the like.

In one aspect of the invention, an interventricular distance measurement mode is entered periodically by the IMD wherein distance measurements between two sites are made during the ventricular contraction and relaxation phases of the heart cycle that are indicative of the instantaneous heart volume and that are representative of the mechanical performance of the ventricles. The first and second ventricular sites preferably comprise right ventricular (RV) and left ventricular (LV) pace/sense electrode sites, and RV event and LV event signals are sensed at the RV and LV pace/sense electrodes.

The distance measurements are made using a magnetic field sensor implanted at a sensor site in or on one of the RV or LV and a magnet implanted at a magnet site in relation to the other of the LV and RV sufficiently spaced at a distance that fluctuates with expansion and contraction of the RV and LV, particularly the LV. The magnetic field sensor provides a sensor output signal having a signal magnitude proportional to the magnetic field strength of the magnet. The contraction and relaxation of the ventricles over the heart cycle causes the magnetic field strength and the sensor output signal magnitude to fluctuate as the distance between the magnet and the magnetic field sensor fluctuates over the heart cycle. The sensor output signal can be calibrated to provide a distance data value of the instantaneous distance between the magnet and the magnetic field sensor.

The IMD preferably includes electrogram (EGM) sensing capabilities for sensing the PQRST complex of the EGM and deriving a ventricular sense (VS) event signal from the R-wave and may include other sensors, e.g. a blood pressure sensor. A single distance data value or a series of distance data values can be measured within a heart cycle timed from a VS event or a pressure trigger event. The data values can be continually obtained from the magnetic field sensor and or measured periodically upon satisfaction of other defined measurement criteria and stored in IMD memory registers or uplink telemetry transmitted to an external medical device for storage and signal processing. The distance data values that are measured during a plurality of heart cycles can be processed to derive average distance data values at predetermined points in the heart cycle and maximum and minimum distance data values over one or more heart cycle. The absolute change and the rate of change in the distance between the magnet and the magnetic field sensor indicative of the acceleration of a ventricular contraction can be determined from the set of distance data values. The IMD can be made to operate in one or more defined operating mode during the measurement and processing of the distance data values. The measured distance data values as well as related data including a date and time stamp of the measurement event, the prevailing heart rate, and the activity level of the patient or other indicator of physiologic need for cardiac output can be stored in IMD memory for subsequent analysis or concurrent uplink telemetry to an external medical device.

Trend data evidencing changes in the physical distance between the first and second ventricular sites or the strength or rate of contraction and expansion gathered over a period of days, weeks, and months provides a valuable indication as to whether the heart failure state is improving, worsening or staying about the same. The present invention can be advantageously employed in an implantable monitor or in any of the known pacing systems, typically DDD and DDDR pacing systems, having data storage and telemetry capabilities.

The present invention is preferably embodied in a multi-site, cardiac pacing system specifically implanted for treating heart failure having memory for storing data and wherein a pacing escape interval is timed out from a VS event or a ventricular pace (VP) pulse to trigger delivery of one or more bi-ventricular pacing therapy. VP pulses are selectively delivered to first and second ventricular sites synchronously within a V-V pace delay at a predetermined pacing rate so as to ensure that the synchronous depolarizations of the right and left ventricles is optimized to maximize cardiac output. The pacing system is preferably programmable to operate in one of a plurality of pacing modes.

In a demand pacing mode, a VS event detected during the time-out of the pacing escape interval at one of the first and second ventricular sites terminates the pacing escape interval and causes a VP pulse to be delivered to the other of the first and second ventricular sites after a VS-VP pace delay. If the pacing escape interval times out without a VS event occurring, the pacing escape interval is terminated causing a VP pulse to be delivered to the both of the first and second ventricular sites separated by a VP-VP pace delay. And, optionally, the VS-VP pace delay and the VP-VP pace delay can be programmed to be terminated without delivery of the second VP pulse if a VS occurs at the ventricular site before time-out.

In a triggered pacing mode, a VS event detected during the time-out of the pacing escape interval at one of the first and second ventricular sites terminates the pacing escape interval and causes the delivery of a triggered VP pulse (a VS/VP pulse) to that ventricular site and a VP pulse to be delivered to the other of the first and second ventricular sites after a VS/VP-VP pace delay. And, optionally, the VS/VP-VP pace delay can be programmed to be terminated without delivery of the second VP pulse if a VS occurs at the ventricular site before it times out.

Preferably, the multi-site cardiac pacing system further comprises a multi-site, AV sequential, bi-ventricular, cardiac pacing system wherein VP pulses are delivered to the right and left ventricles synchronously within the prevailing one of the above-described V-V pace delays following time-out of an AV delay from a preceding delivered atrial pace pulse or an atrial sense event or upon the occurrence of a non-refractory VS event occurring during the time-out of a V-A pacing escape interval.

In one variation, while the pacing system is operating in its programmed pacing mode, a set of magnetic field measurements can be automatically undertaken to develop the distance data when measurement criteria are satisfied or when a downlink telemetry transmitted command is received to initiate the measurements and uplink telemetry transmit the measurements to the external medical device for processing and display of the distance data. And, the pacing system can be successively in time operated in each of the demand and triggered pacing modes to derive multiple sets of magnetic field measurements to obtain sets of distance data particular to each such pacing mode for comparison purposes.

Thus, the interventricular distance measurement mode is entered periodically wherein distance measurements are made during one or more heart cycle embraced by the detection of VS events and/or delivery of VP pulses at the first and second ventricular sites. The long term performance or efficacy of the particular pacing regimen and the parameters employed, including the pacing escape interval, the AV delay and the particular VS-VP, VS/VP-VP and VP-VP delay can be assessed from trends exhibited by the accumulated distance data values.

In accordance with a further aspect of the invention, the pacing parameters including the AV delay and the V-V pace delays (VS-VP, VS/VP-VP and VP-VP delays) can be optimized by entering an optimization mode. In the optimization mode, each such pacing timing parameter is incrementally increased or decreased over one or more heart cycle, and the corresponding distance data is accumulated and compared. The adjusted pacing timing parameter value that provides the maximum absolute change in distance D ($\Delta D_{MAX}$), or rate of change in distance D, that signifies the greatest amount of contraction of the heart chamber is then retained as the controlling pacing parameter value until the optimization mode is again entered and a more optimal pacing parameter value is determined. The optimization program can also be initiated by a downlink telemetry transmitted command during a telemetry session, and the results uplink telemetry transmitted to the programmer for evaluation by the physician or medical care provider operating the programmer.

Moreover, the mechanical performance of the ventricles is assessed from the measured distance data to provide measurements of stroke volume (as derived from cardiac displacement), contractility (as derived from cardiac velocity), pre-ejection period (as derived from cardiac velocity) and ejection time or ejection fraction (which is related to stroke volume). These measurements can be used to provide hemodynamically optimal pacing therapy while the patient is at rest and to provide hemodynamically optimal rate-responsive pacing therapy. Stroke volume, cardiac contractility, pre-ejection period and ejection time may be used, individually or together in combination, to adjust the parameters of the implantable cardiac stimulating device so that hemodynamically optimal pacing therapy may be provided.

The magnetic field sensor and magnet can also be employed for other purposes in the same pacing system. For example, programmable pacing systems feature programmable pace pulse energy levels that can be set to the minimum safe threshold level that is sufficient to trigger a depolarization or "capture" the heart so that delivered pacing energy is not wasted and battery life is prolonged. In accordance with this aspect of the invention, a ventricular pacing threshold test can be undertaken periodically, either during a telemetry session or automatically, to ascertain the current energy threshold for effecting capture. In this capture detection routine, the ventricular pacing pulse energy is incrementally lowered while the magnetic field sensor is activated. The sensor output signal fluctuates each time that the ventricle is captured and contracts until the point where the applied pace pulse energy falls below the threshold and fails to capture the heart which is indicated by the absence of a corresponding change in the sensor output signal. The threshold energy level is stored in IMD memory along with a newly formulated pace pulse energy level sufficiently higher than the threshold energy level to assure capture during pacing until the next threshold test is initiated.

The magnetic field responsive distance sensor of the present invention offers a number of advantages. The magnetic field permeates a lead body and any tissue encapsulation about it without any attenuation, so the magnetic field sensor can be reliably encased within the lead body and is not subject to drift caused by any ambient influences over time. The magnet can be made of a high strength material that is similarly encased securely within a lead body or a magnet housing and placed at a wide number of locations spaced across the ventricles or other heart chambers but close enough so that its magnetic field can be detected by the magnetic field sensor. The magnetic field sensor and the magnet are inexpensive, easy to position, and reliable over long periods of time.

In order to overcome the disadvantages and limitations of previously known approaches for optimizing pacing therapy, the processing system of the present invention processes the derived cardiac wall motion signals (i.e., cardiac wall velocity and displacement) to produce signals representative of stroke volume, cardiac contractility, pre-ejection period and ejection time.

This summary of the invention and the objects, advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. For example, the invention is disclosed in detail herein in the context of an AV sequential, three chamber or four chamber, pacing system operating in demand, atrial tracking, and triggered pacing modes for restoring synchrony in depolarizations and contraction of left and right ventricles in synchronization with atrial sensed and paced events for treating heart failure and/or bradycardia in those chambers. This embodiment of the invention is programmable to operate as a three or four chamber pacing system having an AV synchronous operating mode for restoring upper and lower heart chamber synchronization and right and left atrial and/or ventricular chamber depolarization synchrony. Or, simply bi-ventricular pacing may be applied to the right and left ventricles.

It should be appreciated that the present invention may be utilized in an implantable monitor to gather data in patients suffering various forms of heart failure. The system of the present invention can also may be incorporated into an anti-tachyarrhythmia system including specific high rate pacing and cardioversion shock therapies of typical ICDs for providing staged therapies to treat a diagnosed tachyarrhythmia and optionally including any of the described bradycardia pacing systems.

It will be therefore understood that the various uses of the dimension signals derived employing the system of the present invention described herein can be employed separately or in various combinations in these complex multi-site monitoring, pacing and/or ICD systems and can alternatively be used in simpler dual chamber and single chamber pacemakers, monitors and ICDs which can constitute subsets of the components of this illustrated embodiment of the invention.

Figure 1:
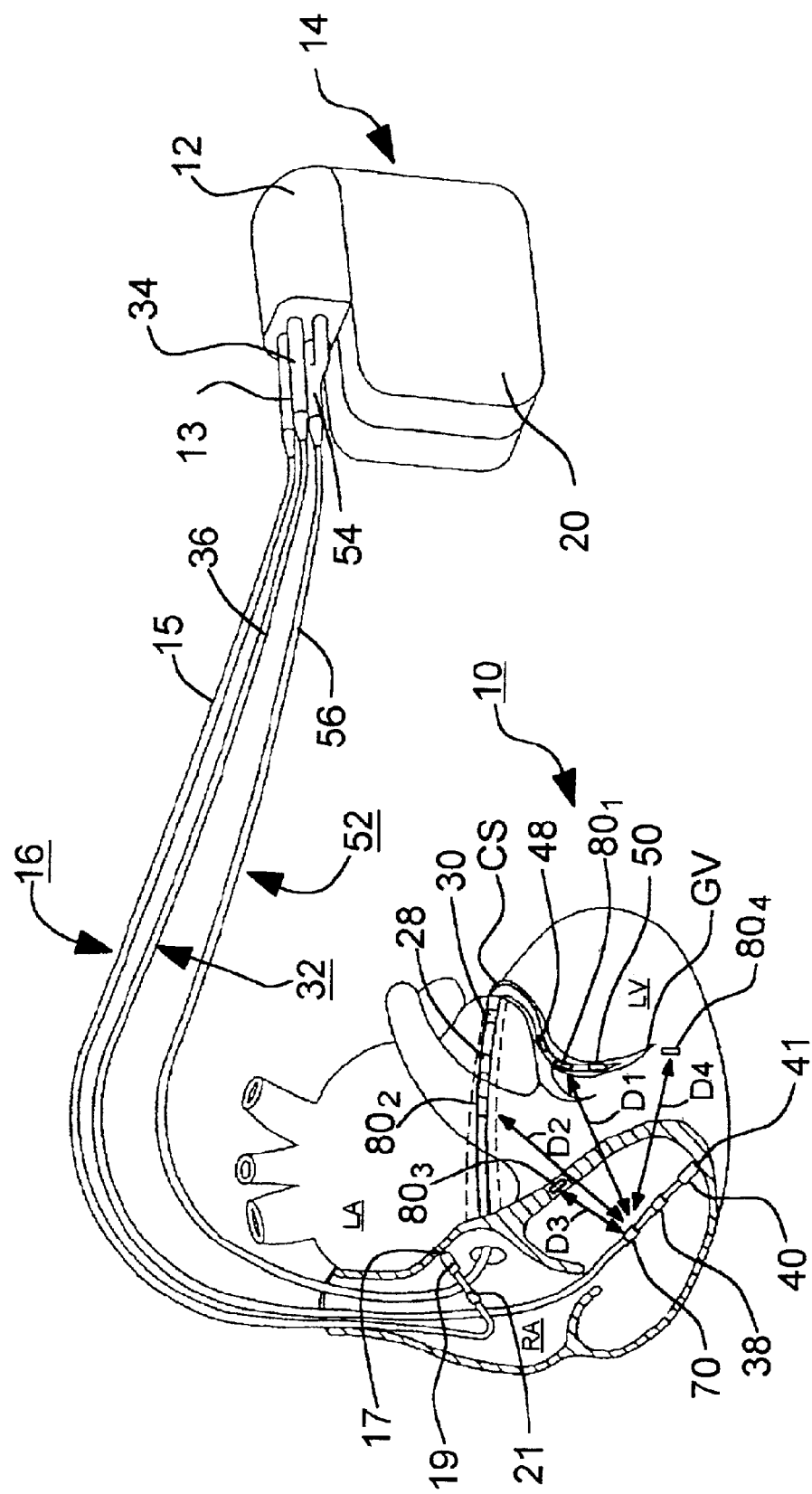
FIG. 1 is a schematic diagram depicting a multi-channel, atrial and bi-ventricular, monitoring/pacing IMD in which the present invention is preferably implemented.

In FIG. 1, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the great vein (GV) that extends further inferiorly into branches of the GV. The cardiac cycle commences normally with the generation of the depolarization impulse at the SA Node in the right atrial wall and its transmission through the atrial conduction pathways of Bachmann's Bundle and the Internodal Tracts at the atrial level into the left atrial septum. The RA depolarization wave reaches the atrio-ventricular (AV) node and the atrial septum within about 40 msec and reaches the furthest walls of the RA and LA within about 70 msec, and the atria complete their contraction as a result. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node is distributed inferiorly down the bundle of His in the intraventricular septum after a delay of about 120 msec. The depolarization wave reaches the apical region of the heart about 20 msec later and is then travels superiorly though the Purkinje Fiber network over the remaining 40 msec. The aggregate RV and LV depolarization wave and the subsequent T-wave accompanying re-polarization of the depolarized myocardium are referred to as the QRST portion of the PQRST cardiac cycle complex when sensed across external ECG electrodes and displayed. When the amplitude of the QRS ventricular depolarization wave passing between a bipolar or unipolar pace/sense electrode pair located on or adjacent the RV or LV exceeds a threshold amplitude, it is detected as a sensed R-wave. Although the location and spacing of the external ECG electrodes or implanted unipolar ventricular pace/sense electrodes has some influence, the normal R-wave width does not exceed 80 msec in width as measured by a high impedance sense amplifier. A normal near field R-wave sensed between closely spaced bipolar pace/sense electrodes and located in or adjacent the RV or the LV has a width of no more than 60 msec as measured by a high impedance sense amplifier.

The typical normal conduction ranges of sequential activation are also described in the article by Durrer et al., entitled "Total Excitation of the Isolated Human Heart", in *CIRCULATION* (Vol. XLI, pp. 899–912, June 1970). This normal electrical activation sequence becomes highly disrupted in patients suffering from advanced CHF and exhibiting IACD, LBBB, RBBB, and/or IVCD. These conduction defects exhibit great asynchrony between the RV and the LV due to conduction disorders along the Bundle of His, the Right and Left Bundle Branches or at the more distal Purkinje Terminals. Typical intra-ventricular peak—peak asynchrony can range from 80 to 200 msec or longer. In RBBB and LBBB patients, the QRS complex is widened far beyond the normal range to from >120 msec to 250 msec as measured on surface ECG. This increased width demonstrates the lack of synchrony of the right and left ventricular depolarizations and contractions. The corresponding mechanical delay can be determined in accordance with the present invention.

The method and apparatus of the present invention can be provided within a three or four chamber pacing system that can be programmed to restore the depolarization sequence and the synchrony between upper and lower and right and left heart chambers that contributes to adequate cardiac output. This restoration is effected through providing optimally timed cardiac pace pulses to the RA and/or LA and, after the AV delay, to the RV and LV as necessary and to account for the particular implantation sites of the pace/sense electrodes in relation to each heart chamber while maintaining AV synchrony. The present invention can be employed to obtain data related to the mechanical function of the heart to aid in the assessment of the efficacy of the programmed pacing mode and parameter values and the progression or regression of heart failure.

Therefore, FIG. 1 also shows a schematic representation of an implanted, four chamber cardiac pacemaker of the above noted types for restoring AV synchronous contractions of the atrial and ventricular chambers and simultaneous or sequential pacing of the right and left ventricles. The pacemaker IPG 14 is implanted subcutaneously in a patient's body between the skin and the ribs. Three endocardial leads 16, 32 and 52 connect the IPG 14 with the RA, the RV and both the LA and the LV, respectively. Each lead has two electrical conductors and at least one pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar pace/sense electrode combinations for pacing and sensing functions, particularly sensing far field signals, e.g., a far field R-wave (FFRS), or bipolar pace/sense electrodes. The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12. The in-line connector 13 is coupled to an RA lead conductor pair within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA).

Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing. Endocardial RV lead 32 is transvenously advanced through the SVC and the RA and into the RV where its distal tip RV pace/sense electrode 40 is fixed in place in the apex by a conventional distal attachment mechanism 41. The RV lead body 36 can also support an indifferent ring-shaped pace/sense electrode 38 for bipolar pacing and sensing through a pair of RV1 lead conductors extending through the lead body 36. Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing, particularly of the far field R-wave.

In this illustrated embodiment, a multi-polar, endocardial CS lead 52 is advanced through the superior vena cava (SVC), the RA, the ostium of the coronary sinus (CS), the CS itself, and into a coronary vein descending from the CS, such as the great vein (GV). The distal pace/sense electrodes 48 and 50 are thus located deep in the GV alongside the LV to allow the depolarization of the LV to be detected and to allow pacing pulses to be delivered to the LV simultaneously with or in timed relation with the delivery of pacing pulses of the RV. In the illustrated four chamber or channel embodiment, LV CS lead 52 bears proximal LA CS pace/sense electrodes 28 and 30 positioned along the CS lead body 56 to lie in the larger diameter CS adjacent the LA. Typically, LV CS leads and LA CS leads do not employ any fixation mechanism and instead rely on the close confinement within these vessels to maintain the pace/sense electrode or electrodes at a desired site.

The LV CS lead 52 is formed with a multiple conductor lead body 56 coupled at the proximal end connector 54 fitting into a bore of IPG connector block 12. A small diameter lead body 56 is selected in order to lodge the distal LV CS pace/sense electrode 50 deeply in a vein branching inferiorly from the great vein GV. In this case, the CS lead body 56 would encase an electrically insulated LA lead conductor pair extending distally from connector elements of a dual bipolar connector 54 to the more proximal LA CS pace/sense electrodes 28 and 30 and an electrically insulated LV lead conductor pair extending distally from connector elements of dual bipolar connector 54 to the more distal LV CS pace/sense electrodes 48 and 50. It will be understood that LV CS lead 52 could bear a single LA CS pace/sense electrode 28 and/or a single LV CS pace/sense electrode 50 that are paired with the IND_CAN electrode 20 or the ring electrode 21 for pacing and sensing in the LA and LV, respectively.

It will be understood that the present invention can be incorporated into a pacing and/or monitoring system that does not employ this particular illustrated arrangement of leads and pace/sense electrodes in relation to the RA, RV, LA and LV. The present invention is directed to detecting the contraction of the ventricles, particularly the LV, deriving signals representing the physical contraction or expansion of the ventricles, particularly the LV, throughout the heart cycle or cycles or at a particular point in the heart cycle or heart cycles, processing and storing the derived signals as described further below. The detection of the occurrence and force of the contraction and expansion of the ventricles is effected by measuring a magnetic field varying in strength with the contraction and expansion.

In accordance with this aspect of the present invention, a magnetic field strength sensitive semiconductor device, sensor or means is implanted at one point in or on a heart chamber and a magnetic field generator is implanted at another position in or on a heart chamber. The magnetic field strength sensitive semiconductor device, sensor or means preferably comprises a Hall effect device 70 that consists of a semiconductor chip which, powered by the IPG 14, is traversed by a current of constant strength. The Hall voltage that is influenced by the strength of the applied magnetic field is tapped off at right angles to the direction of the flowing current as a measured signal from which the actual or relative distance from the magnet can be calculated. A magnetoresistor or magnetic diode exhibiting a semiconducting resistance proportional to an applied magnetic field strength can be used instead as the Hall effect device. For simplicity, these and equivalent magnetic field sensitive devices or means or sensors are collectively referred to illustrated by the Hall effect device 70 providing a Hall effect output signal varying with applied magnetic field strength in this description of the preferred embodiments. The magnetic field generator is preferably a permanent magnet (collectively 80) that is sufficiently distanced at a nominal distance D from the Hall effect device 70 so that the bulk of the heart chamber of interest is between them.

In FIG. 1, magnets $80_1$, $80_2$, $80_3$, and $80_4$ are depicted at exemplary alternative magnet locations or sites in relation to the Hall effect device 70 that is preferably located at a sensor site in the RV and separated from the magnet sites of magnets $80_1$, $80_2$, $80_3$, and $80_4$ by respective distances D1, D2, D3, and D4. Of course, only one such permanent magnet 80 would be implanted at a distance from the Hall effect device 70 in practice, and for convenience is referred to herein as magnet 80 at distance D unless otherwise called out. The magnet 80 is sufficiently close to the Hall effect device so that the magnetic field influences the magnitude of a voltage developed (or resistance changed) across the Hall effect device 70 as a current is applied to it from a signal generator in the IPG. The contraction and expansion of one or more heart chamber causes the distance D between the magnet and sensor sites and the corresponding strength of the magnetic field to vary, whereby a voltage is developed on the current passing through the Hall effect device 70.

The Hall effect device 70 is preferably conveniently incorporated within a distal segment of the lead body 36 of RV lead 32 to be located within the RV after the distal attachment mechanism 41 is attached to or lodged in the ventricular apex. The Hall effect device 70 can be supported within a cylindrical non-magnetic tube sandwiched between an inner tubular electrode and an outer tubular electrode and fitted around the lead body 36. A pair of lead conductors (RV2 in FIG. 2) extend from the Hall effect device 70 through the lead body 36 to the lead connector 34 fitting into a multi-polar bore of IPG connector block 12. The locations of the Hall effect device 70 and magnet 80 could be transposed from those depicted in FIG. 1, and the Hall effect device could be incorporated into the LV CS lead 52 or within a separate lead that is introduced into the CS and GV, and employed with any other magnet located sufficiently far away so that the contraction and expansion of the heart chamber of interest can be determined.

In this regard, it is necessary to avoid a placement directly across the septum or a heart wall as described in the above-referenced '540 patent wherein the compliance of the heart wall is monitored to detect any loss of compliance characteristic of rejection of a heart transplant. Such a placement would not provide a measure of the timing or strength of contraction of the bulk of the ventricles.

In one embodiment of the present invention, the permanent magnet $80_1$ is incorporated within a distal segment of the lead body 56 of LV CS lead 52 to be located alongside the LV at a distance D1 across the RV and LV from the Hall effect device 70. Therefore, the distance D1 changes as the LV contracts in systole and expands in diastole, changing the magnitude of the Hall effect output signal and allowing the changes in D1 to be determined.

Alternatively, a permanent magnet $80_2$ is incorporated within a more proximal segment of the lead body 56 of LV CS lead 52 to be located alongside the LA at a distance D2 from the Hall effect device 70. The permanent magnet $80_2$ could alternatively be located more proximally on lead body 56 to locate it in the RA or SVC. Or, a permanent magnet 80 could be located on the RA lead body 15 to locate it in the RA or SVC. Therefore the distance D2 changes as the RA and RV contract and expand and to some extend as the ventricles contract, changing the magnitude of the Hall effect output signal and allowing the changes in D2 to be determined.

Moreover, a permanent magnet $80_3$ could be implanted within or attached to a thick section of the interventricular septum separating the RV and LV at a distance D3 from the Hall effect device 70. Such a placement could be effected by providing the magnet $80_3$ through a delivery catheter lumen or at the distal end of a detachable delivery catheter advanced to the site and fixing the magnet $80_3$ at the site employing an attachment screw or other fixation mechanism. Therefore, the distance D3 changes as the septum moves while the RV and LV contract and expand, changing the magnitude of the Hall effect output signal and allowing the changes in D3 to be determined.

While the Hall effect device 70 and the magnet 80 could be surgically implanted outside the heart on the RV and LV epicardium, for example, doing could involve invasive surgery that could be dangerous to a patient suffering advanced heart failure. Moreover, placing the leads carrying the pace/sense electrodes and at least the Hall effect device is not as convenient as transvenously placing the leads depicted in FIG. 1. However, the Hall effect device 70 and magnet 80 could be implanted epicardially if such surgery is necessitated for other reasons or by microsurgical implantation techniques. In this regard, the magnet 80 could be implanted attached to the left ventricular epicardium or into the myocardium as illustrated by magnet $80_4$ in FIG. 1 employing minimally invasive microsurgical techniques. The distance D4 changes as the RV and LV contract and expand, changing the magnitude of the Hall effect output signal and allowing the changes in D4 to be determined.

Thus, a variety of ways of placing the Hall effect device 70 and permanent magnet 80 are disclosed and equivalents will be apparent to those of skill in the art. The use of permanent magnets instead of electromagnets powered by the IPG 12 is preferred due to size and energy consumption issues that arise in fabricating strong enough electromagnets, implanting them with respect to the heart chamber of interest, and providing adequate power from the IPG battery. The distances D1, D2, D3, D4 vary during the heart cycle, depending upon the instantaneous state of contraction or relaxation of the heart chambers.

In particular, the distances D1, D2, D3, D4 change with contraction and expansion or relaxation of the heart during the heart cycle, and the change in distance ΔD over the heart cycle causes a time varying signal to be developed by each Hall effect device associated with distances D1, D2, D3, D4 as described above, that is sampled at a sample rate. During relaxation or asystole, the distances D1, D2, D3, D4 would be the greatest, and the corresponding signal developed by each Hall effect device would have the lowest amplitude. At varying times during contraction of the heart or asystole, the distances D1, D2, D3, D4 would be the smallest, and the corresponding signal developed by each Hall effect device would have the highest amplitude. The peak difference in signal amplitude over a heart cycle thus is an indicator of the peak change in dimension or ΔD. The rate of change of the difference in signal amplitudes can also be determined.

Thus, both the occurrence of a contraction and a measure of the amount of contraction of a heart chamber traversed by one of the distances D1, D2, D3, D4 can be ascertained and quantified as a measure of mechanical performance. It can be assumed that the relative strength of contraction of a heart chamber can be determined from the absolute change in dimension ΔD as well as the rate of change in the difference in signal amplitudes. An increase in the absolute change in dimension ΔD as well as the rate of change in the difference in signal amplitudes signifies a more forceful contraction of a heart chamber and can be considered to constitute an improvement in cardiac output.

The occurrence of a contraction can be employed to detect electromechanical dissociation during pacing or arrhythmias, differentiate hemodynamically significant and insignificant ventricular tachycardias, monitor cardiac output, provide confirmation of capture or loss of capture for autocapture algorithms, adjust rate responsive pacing based on myocardial contractility, detect periods of syncope, detect or classify atrial and ventricular tachyarrhythmias, automatically adjust sense amplifier sensitivity based on detection of mechanical events, and be employed as a factor in determining pacemaker mode switching, determining the need for fast and aggressive versus slower and less aggressive anti-tachyarrhythmia therapies, or determining the need to compensate for a weakly beating heart after therapy delivery, and the like.

Figure 2:
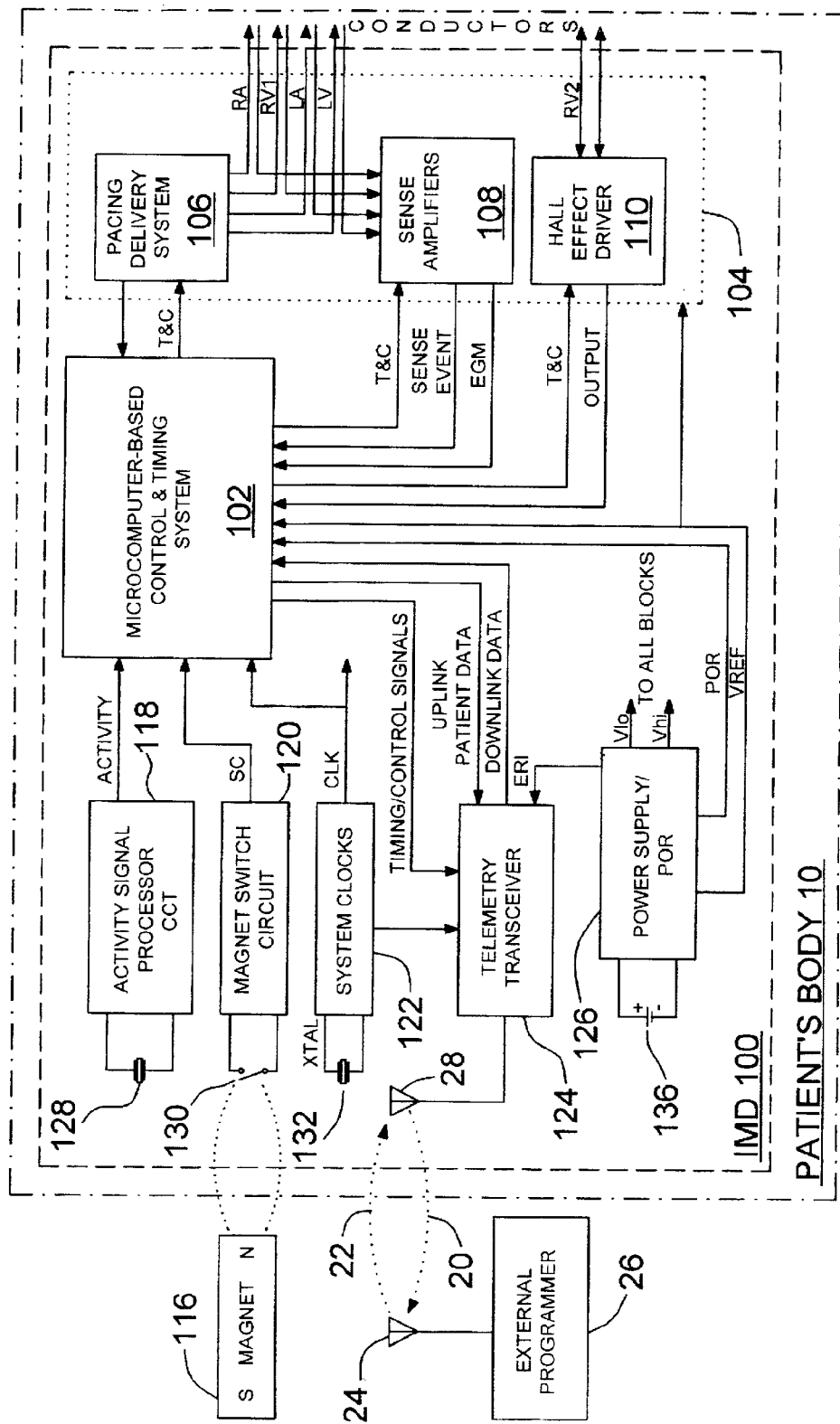
FIG. 2 is a simplified block diagram of one embodiment of IMD circuitry and associated leads employed in the system of FIG. 1 enabling selective therapy delivery and/or monitoring of contraction and expansion of the ventricles during the paced or intrinsic heart cycle to develop data representing changes in mechanical function.

FIG. 2 depicts a system architecture of an exemplary multi-chamber monitor/therapy delivery system or IMD 100 implanted into a patient's body 10 that provides delivery of a therapy and/or monitors a physiologic condition through the RA, LA, RV1 and LV lead conductor pairs. The IMD 100 has a system architecture that is constructed about a microcomputer-based control and timing system 102 that varies in sophistication and complexity depending upon the type and functional features incorporated therein. The functions of microcomputer-based multi-chamber monitor/therapy delivery system control and timing system 102 are controlled by firmware and programmed software algorithms stored in RAM and ROM including PROM and EEPROM and are carried out using a CPU, ALU, etc., of a typical microprocessor core architecture. The microcomputer-based multi-chamber monitor/therapy delivery system control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of multi-chamber IMD 100 can be accomplished with dedicated circuit hardware or state machine logic rather than a programmed micro-computer.

The multi-chamber IMD 100 also typically includes patient interface circuitry 104 for conducting signals between the monitor/therapy delivery system control and timing system 102 and the above-described Hall effect device 70 and the pace/sense electrode pairs located at specific sites of the patient's heart chambers to derive heart failure parameters and to deliver multi-chamber pacing therapies, particularly AV synchronous, bi-atrial and bi-ventricular pacing therapy to the heart chambers. The patient interface circuitry 104 therefore comprises a pacing stimulation delivery system 106 (which may be eliminated in a monitor IMD), a sense amplifiers circuit 108 (both coupled with the above-described RA. RV1, LA and LV lead conductor pairs) and a Hall drive current generator and voltage detector 110 coupled to the LV lead conductor pair extending to the Hall effect device 70. The patient interface circuitry 104 can be configured to include circuitry for delivering cardioversion/defibrillation shocks and/or cardiac pacing pulses delivered to the heart or cardiomyostimulation to a skeletal muscle wrapped about the heart. A drug pump for delivering drugs into the heart to alleviate heart failure or to operate an implantable heart assist device or pump implanted in patients awaiting a heart transplant operation can also be incorporated into the multi-chamber IMD 100. Moreover, patient interface circuitry 104 can be configured to process physiologic signals, including blood pressure, blood pH and blood temperature, respiration related impedance signals, and any other physiologic signals of interest.

A battery provides a source of electrical energy to power the multi-chamber IMD 100 and to power any electromechanical devices, e.g., valves, pumps, etc. of a substance delivery multi-chamber monitor/therapy delivery system, or to provide electrical stimulation energy of an ICD shock generator, cardiac pacing pulse generator, or other electrical stimulation generator associated therewith. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF sources, current sources, an elective replacement indicator (ERI) signal, and, in the case of an ICD, high voltage power Vhi to the therapy delivery system 106. Not all of the conventional interconnections of these voltages and signals are shown in FIG. 2.

Virtually all current electronic multi-chamber monitor/therapy delivery system circuitry employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 2, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers may be used for storing data compiled from sensed cardiac activity and/or relating to device operating history or sensed physiologic parameters for uplink telemetry transmission on receipt of a retrieval or interrogation instruction via a downlink telemetry transmission. The criteria for triggering data storage can also be programmed in via downlink telemetry transmitted instructions and parameter values The data storage is either triggered on a periodic basis or by detection logic within the sense amplifiers circuit 108 upon satisfaction of certain programmed-in event detection criteria. In some cases, the multi-chamber IMD 100 includes a magnetic field sensitive switch 130 that closes in response to a magnetic field, and the closure causes a magnetic switch circuit to issue a switch closed (SC) signal to control and timing system 102 which responds in a magnet mode. For example, the patient may be provided with a magnet 116 that can be applied over the subcutaneously implanted multi-chamber IMD 100 to close switch 130 and prompt the control and timing system to deliver a therapy and/or store physiologic episode data when the patient experiences certain symptoms. In either case, event related data, e.g., the date and time, may be stored along with the stored periodically collected or patient initiated physiologic data for uplink telemetry in a later interrogation session.

Uplink and downlink telemetry capabilities are provided in the multi-chamber IMD 100 to enable communication with either a remotely located external medical device or a more proximal medical device on the patient's body or another multi-chamber monitor/therapy delivery system in the patient's body. The stored physiologic data of the types described above as well as real-time generated physiologic data and non-physiologic data can be transmitted by uplink RF telemetry from the multi-chamber IM1 100 to the external programmer or other remote medical device 26 in response to a downlink telemetry transmitted interrogation command. The real-time physiologic data typically includes real time sampled signal levels, e.g., intracardiac electrocardiogram amplitude values, and sensor output signals including pressure and the distance signals D derived from the output signals of the Hall effect driver circuit 110. The non-physiologic patient data includes currently programmed device operating modes and parameter values, battery condition, device ID, patient ID, implantation dates, device programming history, real time event markers, and the like. In the context of implantable pacemakers and ICDs, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies. The multi-chamber monitor/therapy delivery system thus develops a variety of such real-time or stored, physiologic or non-physiologic, data, and such developed data is collectively referred to herein as "patient data".

The sense amplifiers circuit 108 includes at least one electrical sense amplifier circuit for amplifying, processing and in some cases detecting sense events from characteristics of the electrical EGM signal across the selected pace/sense electrode pair. The sense amplifiers circuit 108 in multi-chamber monitor/therapy delivery systems providing dual chamber or multi-site or multi-chamber monitoring and/or pacing functions includes a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave or R-wave, respectively and providing an RA-SENSE, RV-SENSE, LA-SENSE and/or LV-SENSE event signal to the control and timing system 102. Timing and control system 102 responds in accordance with its particular operating system to deliver or modify a pacing therapy, if appropriate, or to accumulate data for uplink telemetry transmission or to provide a Marker Channel® signal in a variety of ways known in the art.

The pacing stimulation delivery system 106 preferably comprises an RA pacing output pulse generator, an RV pacing pulse generator, an LV pacing pulse generator and optionally an LA pacing pulse generator selectively coupled in each case to an RA, RV, LV and LA pace electrode pair which can be programmably selected as described above. For example, the RA pacing output pulse generator can be coupled to the RA lead conductors, the RV pacing pulse generator can be coupled to the RV1 lead conductors, the LV pacing pulse generator can be coupled to the LV lead conductors, and the LA pacing pulse generator can be coupled to the LA lead conductor pair for bipolar pacing in relation to each chamber. Two, three or four chamber synchronized pacing is effected employing combinations of these pacing pulse generators and following a pacing timing algorithm carried out by microcomputer-based timing and control system 102 in a manner disclosed in commonly assigned, U.S. Pat. No. 5,902,324.

One aspect of the present invention seeks to provide trend data to the physician to advise the physician as to the current state of heart failure as manifested by changes in the periodically measured distance D of FIG. 1 over one or more heart cycle. A heart cycle can constitute the time period comprising the V-A escape interval followed by the AV delay and bracketed by consecutive VS events starting and terminating the time period or VP pulses starting and terminating the time period.

Another aspect of the invention seeks to optimize the pacing parameters of the programmed pacing mode to maximize the contraction of the LV as evidenced by the changes in the above-described distances.

In either case, the Hall effect driver 110 is enabled during the heart cycle or cycles by timing and control signals from the microcomputer-based timing and control system 102 to energize the Hall effect device 70. The instantaneous changes in the Hall voltage developed by changes in the magnetic field are sampled by the Hall effect driver 110 at a predetermined sample rate, and the resulting sensor output signals are conveyed to the microcomputer-based timing and control system 102 for storage and/or processing to effect one of the processes stated above.

Normal Pacing Modes:

The possible multi-chamber pacing modes of IMD 100 are depicted in the flow chart of FIGS. 3 through 5B and described as follows. The particular operating modes of the present invention are implemented as a programmed or hard-wired sub-set of the possible operating modes. The AV delay is started in step S100 when a P-wave outside of refractory is sensed across the selected atrial sense electrode pair during the V-A escape interval (an A-EVENT) as determined in step S134 or an A-PACE pulse is delivered to the selected atrial pace electrode pair in step S118. The AV delay can be a PAV or SAV delay, depending upon whether it is started on an A-PACE or an A-EVENT, respectively, and is timed out by the an SAV/PAV delay timer. The SAV or PAV delay is terminated upon a non-refractory RV-EVENT or LV-EVENT output by a ventricular sense amplifier prior to its time-out.

Post-event timers within microcomputer-based control and timing system 102 are started to time out the post-ventricular time periods and the TRIG_PACE window, and a V-A escape interval timer within microcomputer-based control and timing system 102 is started to time out the V-A escape interval in step S104 if the SAV or PAV delay times out in step S102 without the detection of a non-refractory RV-EVENT or LV-EVENT. The TRIG_PACE window inhibits triggered pacing modes in response to a sense event occurring too early in the escape interval.

Either a programmed one or both of the RV-PACE and LV-PACE pulses are delivered in step S106 (as shown in the flow chart of FIG. 4) to selected RV and LV pace electrode pairs, and the V-A escape interval timer is timed out in step S116. When both of the RV-PACE and LV-PACE pulses are delivered, the first is referred to as V-PACE1, the second is referred to as VPACE2, and they are separated by a VP-VP delay. As described in greater detail below in reference to FIGS. 5A–5B, if a bi-ventricular pacing mode is programmed in step S106, it can be selectively programmed in a left-to-right or right-to-left ventricle pacing sequence wherein the first and second delivered ventricular pace pulses are separated by separately programmed VP-VP delays. The VP-VP delays are preferably programmable between about 4 msec and about 80 msec.

The baseline or lower rate SAV, PAV and VP-VP delays are initially selected to optimize LA function and LV cardiac output in a patient work-up, typically while the patient is at rest, as described further below in reference to FIG. 6. However, these time delays and the V-A escape interval can be programmed to be adjusted within programmed upper and lower limits to accommodate the patient's requirements for cardiac output due to exercise as reflected by the ACTIVITY signal output by the activity signal processor circuit. The dimension D data associated with the optimum LA function and LV cardiac output are also collected and stored in IMD memory within microcomputer-based control and timing system 102 during the work-up. The dimension data is periodically collected and stored in IMD memory over weeks or months to reveal any trends in the heart failure state.

Returning to step S102, the AV delay is terminated if an RV-EVENT or LV-EVENT (collectively, a V-EVENT) is generated by the RV sense amplifier or the LV sense amplifier in step S108. The time-out of the V-A escape interval and the post-ventricular time periods are started in step S110 in response to the V-EVENT. In step S112, it is determined whether a ventricular triggered pacing mode is programmed to be operative during the AV delay. A ventricular triggered pacing mode is programmed on, and it is undertaken and completed in step S114 (FIGS. 6A–6B). Any VSP mode that may otherwise be available is programmed off. The time-out of the TRIG_PACE window is commenced in step S113 simultaneously with the timeout of the V-A escape interval and post-event time periods in step S110.

The A-PACE pulse is delivered across the selected RA pace electrode pair in step S118, the AV delay is set to PAV in step S120, and the AV delay is commenced by the AV delay timer if the V-A atrial escape interval is timed out in step S116 without a non-refractory A-EVENT being sensed across the selected pair of atrial sense electrodes. But, the V-A escape interval is terminated if a non-refractory A-EVENT is generated as determined in steps S122 and S134. The ABP and ARP are commenced upon an A-EVENT by post-event timers within microcomputer-based control and timing system 102 in step S134, the AV delay is set to the SAV in step S138, and the SAV delay is started in step S100 and timed out by the SAV/PAV delay timer.

Assuming that the normal activation sequence is sought to be restored, a programmed SAV and PAV delay corresponding to a normal AV conduction time from the AV node to the bundle of His are used or a calculated SAV and PAV delay is calculated in relation to the prevailing sensor rate or sensed intrinsic heart rate and are used by SAV/PAV delay timer 372.

If an RV-EVENT or LV-EVENT (for simplicity, referred to as a V-EVENT) is detected in step S123 during the time-out of the V-A escape interval, then, it is determined if it is a non-refractory V-EVENT or a refractory V-EVENT in step S124. If the V-EVENT is determined to be a non-refractory V-EVENT in step S124, then the TRIG_PACE window is started or restarted, the V-A escape interval is restarted, and the post-ventricular time periods are restarted in step 126.

Figure 5A:
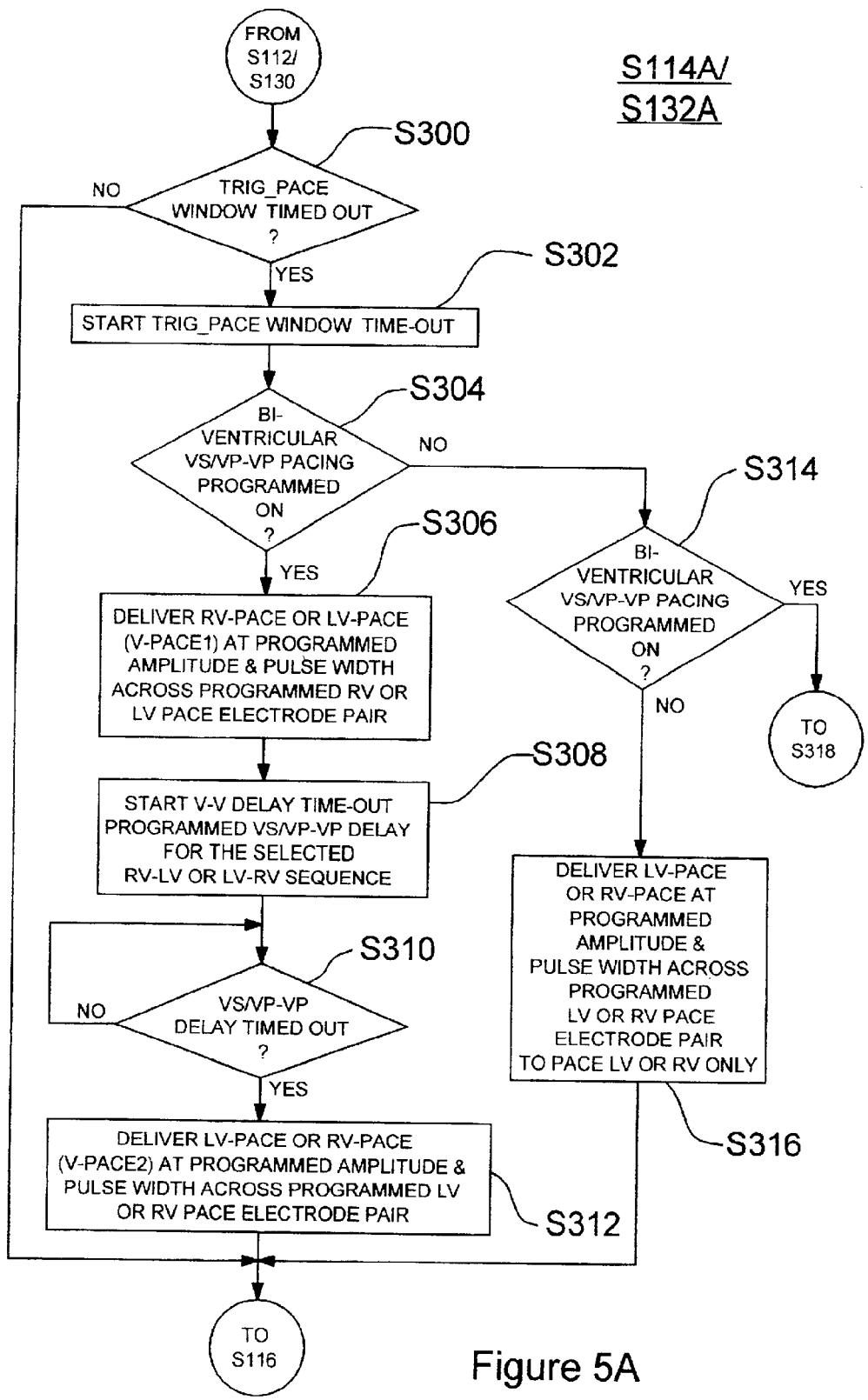
FIGS. 5A–5B is a flow chart illustrating the steps of delivering ventricular pace pulses following a ventricular sense event during the time-out of an AV delay or the V-A escape interval in FIG. 3.
Figure 5B:
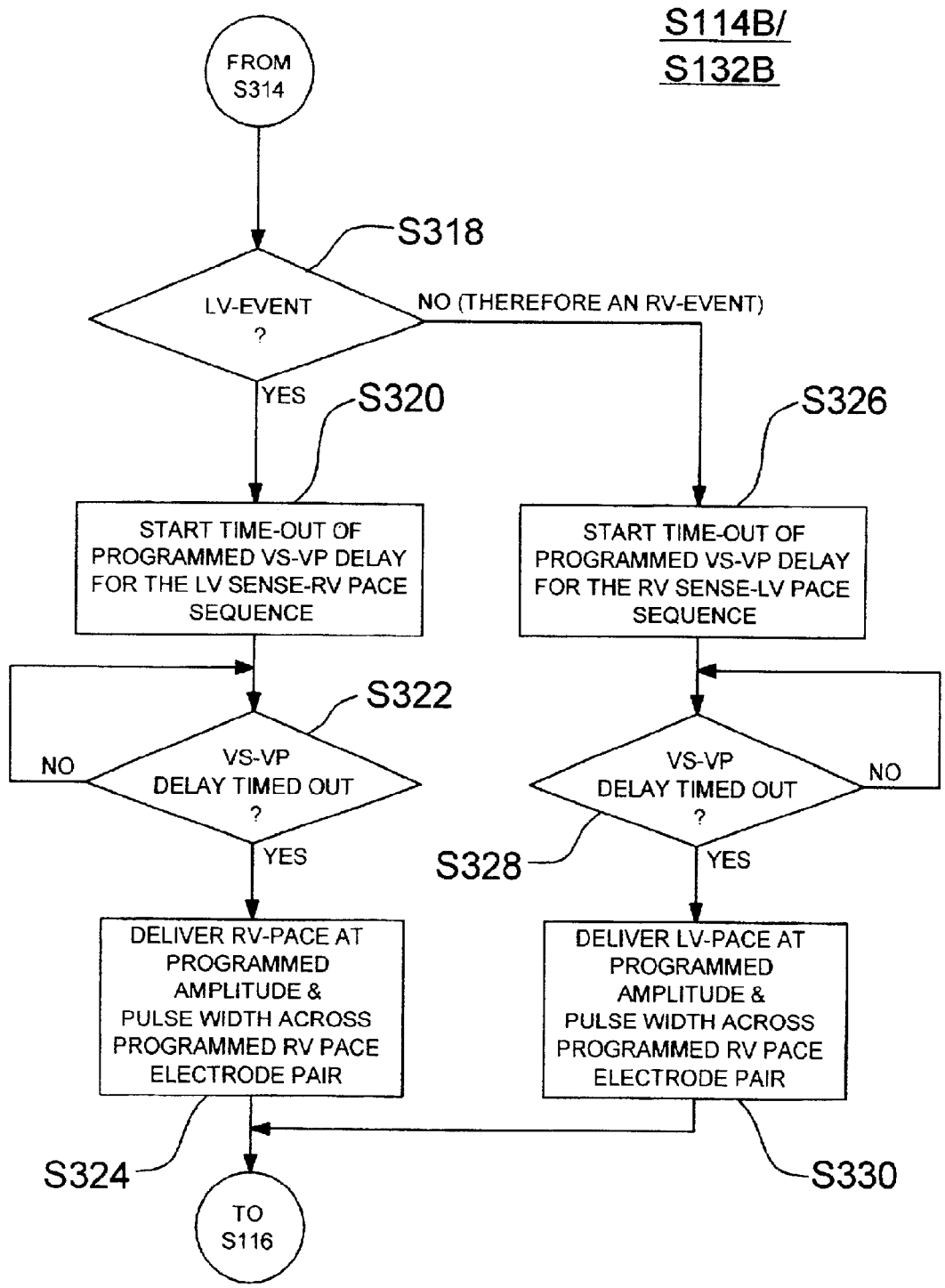

In step S128, it is determined whether a ventricular triggered pacing mode is programmed to be operative during the V-A escape interval. Ventricular triggered pacing during the V-A escape interval is not programmed on or not provided in the pacing system when triggered ventricular pacing is inappropriate for the patient. If ventricular triggered pacing during the V-A escape interval is programmed on, then it is undertaken and completed in step S132 (FIGS. 5A–5B). If ventricular triggered pacing is not programmed on as determined in step S130, then no ventricular pacing is triggered by the sensed non-refractory V-EVENT during the V-A escape interval. Steps S130 and S132 are merely included herein to complete the disclosure of one form of an AV synchronous pacing system in which the present invention may be incorporated. It will be understood that the present invention can be incorporated into an AV synchronous pacing system that does not include steps S130 and S132.

Figure 4:
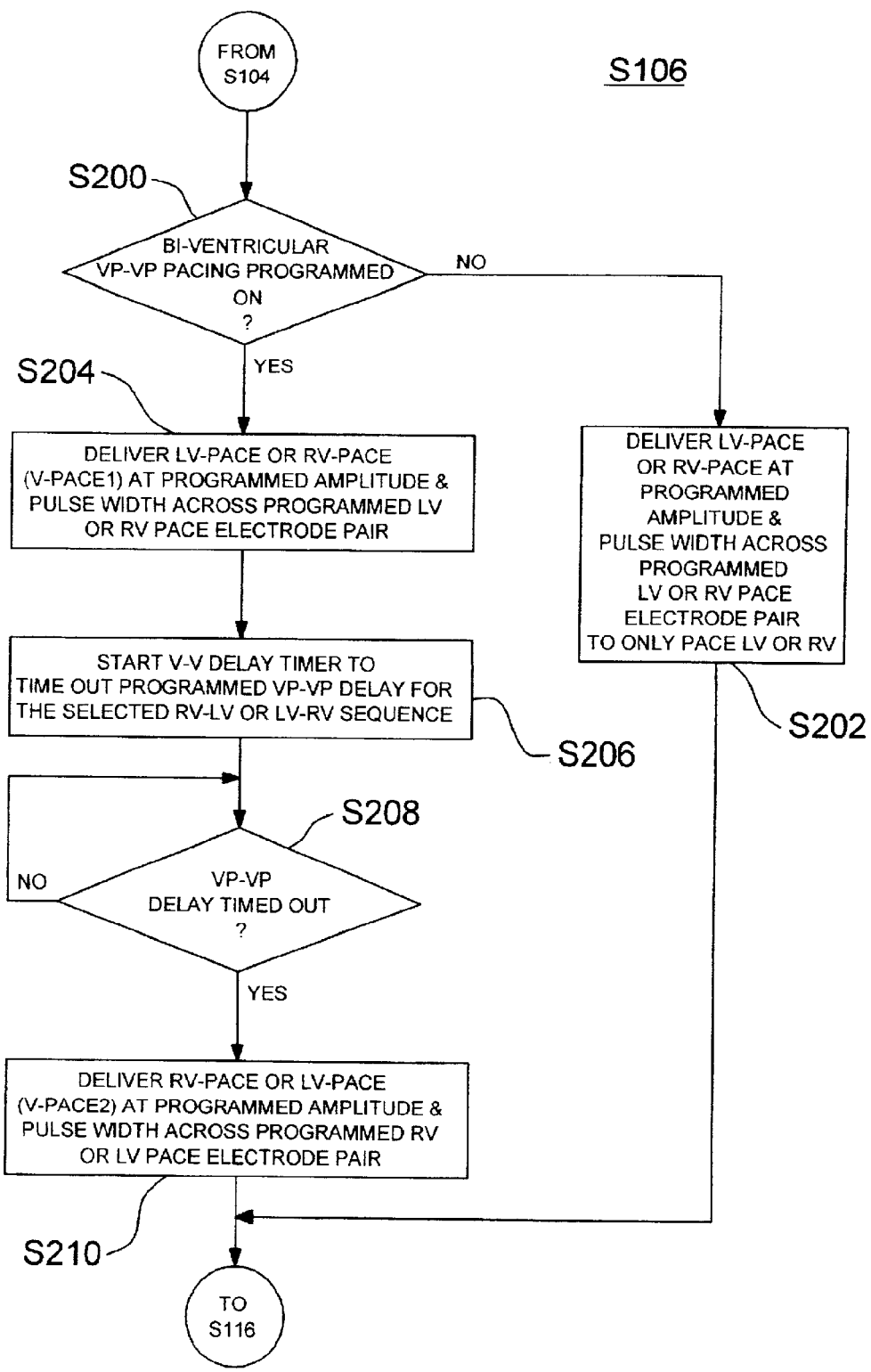
FIG. 4 is a flow chart illustrating the steps of delivering ventricular pace pulses following time-out of an AV delay in FIG. 3.

FIG. 4 depicts the step S106 in greater detail, and FIGS. 5A–5B depict the steps S114 and S132 in greater detail. If a VP-VP pacing mode is programmed on in step S106, it can be selectively programmed in a left-to-right or right-to-left ventricle sequence, wherein the first and second delivered ventricular pace pulses (V-PACE1 and V-PACE2) are separated by separately programmed VP-VP delays. If a bi-ventricular triggered pacing mode is programmed on in either or both of steps S114 and S132, it can be selectively programmed to immediately pace the ventricle from which the V-EVENT is sensed or a fixed or programmed ventricle regardless of where the V-EVENT is sensed with a V-PACE1. Then, the V-PACE2 is generated to synchronously pace the other ventricle after a programmed VS/VP-VP delay. Or, the triggered pacing mode can be selectively programmed in either or both of steps S114 and 132 to only synchronously pace the other ventricle than the ventricle from which the V-EVENT is sensed with V-PACE2 after separately programmable VS-VP delays, depending on the right-to-left or left-to-right sequence. All of these VP-VP, VS/VP-VP, and VS-VP delays are preferably programmable between nearly 0 msec and about 80 msec.

As a practical matter, the minimum VS/VP-VP, and VP-VP delays may be set to one half the system clock cycle in order to avoid simultaneous delivery of RV-PACE and LV-PACE pulses. The pace pulse width is typically programmable between about 0.5 msec and 2.0 msec, and the pace pulse amplitude is typically programmable between 0.5 and 7.5 volts. The system clock provides a full clock cycle of about 8.0 msec. Therefore, the minimum VP-VP delay is set at a half clock cycle or about 4.0 msec.

As shown in FIG. 4, the IMD 100 of FIG. 2 can be programmed to either only deliver a single RV-PACE or LV-PACE (V-PACE1) or the pair of RV-PACE and LV-PACE pulses (V-PACE1 and V-PACE2) separated by the VP-VP delay timed out by a V-V delay timer within microcomputer-based control and timing system 102. If delivery of only a single RV-PACE or LV-PACE is programmed as determined in step S200, then it is delivered in step S202.

If VP-VP pacing is programmed on in step S200, then V-PACE1 is delivered in step S204 in the programmed RV-LV or LV-RV sequence. Again, the RV-PACE pulse is typically delivered across the active RV tip electrode 40 and one of the available indifferent electrodes that is programmed and selected depending upon which are present in the pacing system and the RV pacing vector that is desired as set forth above. And, the LV-PACE pulse is delivered across the active LV pace electrode 50 and a selected indifferent electrode, e.g. pace/sense electrode 48. The V-PACE1 pace pulse is delivered at a programmed pulse energy dictated by the programmed voltage and pulse width.

The V-V delay timer is loaded with the programmed VP-VP delay and starts to time out in step S206. If the RV-PACE pulse is V-PACE1, then a programmed VP-VP delay is timed in V-V delay timer. The LV-PACE pulse is delivered as V-PACE2 in the LV pacing path between the active LV pace/sense electrode 50 and the selected indifferent pace/sense electrode 48 in step S210 after time-out of the programmed VP-VP delay in step S208. Conversely, if the LV-PACE pulse is the first to be delivered (V-PACE1), then a programmed VP-VP delay is timed out in the V-V delay timer. The RV-PACE pulse is then delivered as V-PACE2 typically across the active RV pace/sense electrode 40 and the programmed indifferent pace/sense electrode in step S210 after time-out of the programmed VP-VP delay in step S208.

Figure 3:
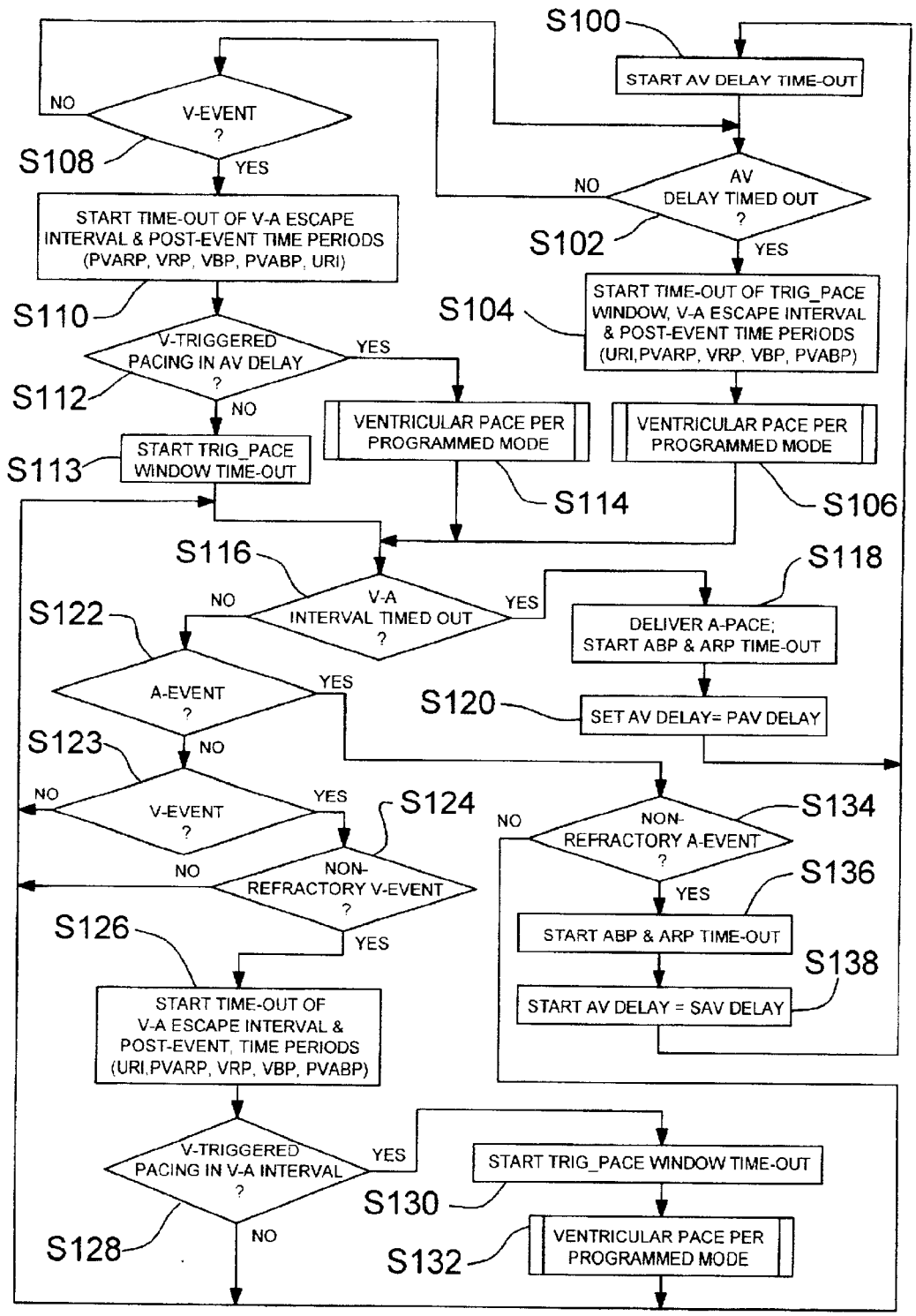
FIG. 3 is a comprehensive flow-chart illustrating the operating modes of the IMD circuitry of FIG. 2 in a variety of AV synchronous, bi-atrial and bi-ventricular pacing modes in accordance with one embodiment of the invention.

FIGS. 5A–5B is a flow chart illustrating the steps S114 and S132 (when provided or programmed on) of FIG. 3 for delivering ventricular pace pulses triggered by a ventricular sense event in step S108 during the time-out of an AV delay or in step S124 during time-out of the V-A escape interval. The sensing of R-waves in the RV and LV can be accomplished employing several RV-SENSE and LV-SENSE sensing axes or vectors including a trans-ventricular sensing vector. A bipolar RV-SENSE vector (RV pace/sense electrodes 38 and 40), a unipolar RV-SENSE vector (RV tip pace/sense electrode 40 and IND_CAN electrode 20), and a unipolar LV-SENSE vector (LV pace/sense electrode 50 and IND_CAN electrode 20), and a trans-ventricular, combined RV-SENSE and LV-SENSE vector (RV pace/sense electrode 40 and LV pace/sense electrode 50) can be programmed. The selection of the sensing vectors would depend upon heart condition and the selection of the pace pulse pathways.

The IMD 100 can be separately programmed in one of three triggered pacing modes designated VS/VP, VS/VP-VP or VS-VP triggered modes for step S114. In the VS/VP triggered pacing mode, a V-PACE1 is delivered without delay upon a RV-EVENT or LV-EVENT to the RV or LV pacing pathway, respectively. In the VS/VP-VP triggered pacing mode, the V-PACE1 is delivered without delay upon a RV-EVENT or LV-EVENT to the selected RV or LV pacing electrode pair, respectively, and a V-PACE2 is delivered to the other of the selected LV or RV pacing electrode pair after the VS/VP-VP delay times out. In the VS-VP pacing mode, a RV-EVENT or the LV-EVENT starts time-out of a VS-VP delay, and a single pace pulse (designated V-PACE2) is delivered to the selected LV or the RV pace electrode pair, respectively, when the VS-VP delay times out.

The TRIG_PACE time window started by a prior V-EVENT or V-PACE must have timed out in step S300 prior to delivery of any triggered ventricular pace pulses. If it has not timed out, then triggered pacing cannot be delivered in response to a sensed V-EVENT. If the TRIG_PACE window has timed out, it is then restarted in step S302, and the programmed triggered pacing modes are checked in steps S304 and S316.

When IMD 100 is programmed in the VS/VP-VP triggered mode as determined in step S304, the non-refractory RV-EVENT or LV-EVENT or collective V-EVENT of indeterminable origin is treated as a single V-EVENT. If the TRIG_PACE window has timed out as determined in step S300, then the single V-EVENT triggers the immediate delivery of a programmed one of the RV-PACE or a LV-PACE as V-PACE1 across the programmed bipolar or unipolar RV and LV pace electrode pair, respectively, in step S306. Thus, V-PACE1 is delivered to a predetermined RV or LV pace electrode pair, regardless of whether a RV-EVENT and LV-EVENT is sensed.

Then, a VS/VP-VP delay is started in step S308 and timed out in step S310. The VS/VP-VP delay is specified as a VP-VP delay when the RV-PACE is V-PACE1 and the LV-PACE is V-PACE2. The VS/VP-VP delay is specified as a VP-VP delay when the LV-PACE is V-PACE1 and the RV-PACE is V-PACE2. The LV-PACE or RV-PACE pulse is delivered at the programmed amplitude and pulse width across the programmed LV or RV pace electrode pair in step S210.

In step S314, it is determined whether the VS-VP triggered pacing mode or the VS/VP triggered pacing mode is programmed. When the IMD 100 is programmed to a single heart chamber VS/VP triggered pacing mode, the RV-EVENT or LV-EVENT triggers the immediate delivery of an RV-PACE or an LV-PACE across a programmed bipolar or unipolar RV or LV pace electrode pair, respectively, in step S316, regardless of whether an RV-EVENT or LV-EVENT was sensed.

When the IMD 100 is programmed to the VS-VP triggered pacing mode, an LV-EVENT as determined in step S318 loads the appropriate VS-VP delay in V-V delay timer in step S320 and starts the VS-VP delay time-out in step S322. The RV-PACE is delivered at its time-out in step S322 (also designated V-PACE2). If an RV-EVENT is determined in step S318, then the appropriate VS-VP delay in V-V delay timer in step S326 and the VS-VP delay is timed out in step S328. The LV-PACE (also designated V-PACE2) is delivered at time-out of the VS-VP delay in step S330.

In all of steps S306, S312, S316, S324 and S330, the LV-PACE pulse is preferably delivered as V-PACE2 in the LV pacing path between the active LV pace/sense electrode 50 and pace/sense electrode 48.

Returning to FIG. 3, the V-A escape interval is timed out in step S116 following the completion of the ventricular pacing mode of FIGS. 6A–6B. If the V-A escape interval times out, then an RA-PACE pulse is typically first delivered across the RA pace electrodes 17 and 19 in step S118, and the AV delay timer is restarted in step S100.

Thus, it will be observed that the multi-site, AV sequential, bi-ventricular cardiac pacing system described above is selectively programmable to provide ventricular pacing pulses delivered to one or both of the RV and LV sites synchronously within a V-V pace delay following time-out of an AV delay from a preceding delivered A-PACE pulse or an A-EVENT (typically, the RA-PACE pulse or the RA-EVENT) and operating in accordance with the steps of: (a) timing an AV delay from a preceding delivered A-PACE pulse or A-EVENT; (b) detecting a V-SENSE at one of a first and second ventricular site within the AV delay and, in response, terminating the AV delay and providing a V-EVENT; (c) delivering a V-PACE1 pulse to a selected one of the first and second ventricular sites upon the time-out of the AV delay or, in a triggered mode, upon the V-SENSE; (d) timing a V-V pace delay comprising one of a VS-VP pace delay from a V-EVENT occurring prior to the time-out of the AV delay or a VP-VP pace delay from the V-PACE1 delivered at the end of the AV delay or a VS/VP-VP pace delay from a triggered V-PACE1; and (e) delivering a V-PACE2 pulse to the other of the first and second ventricular sites upon the time-out of the V-V pace delay.

Figure 6:
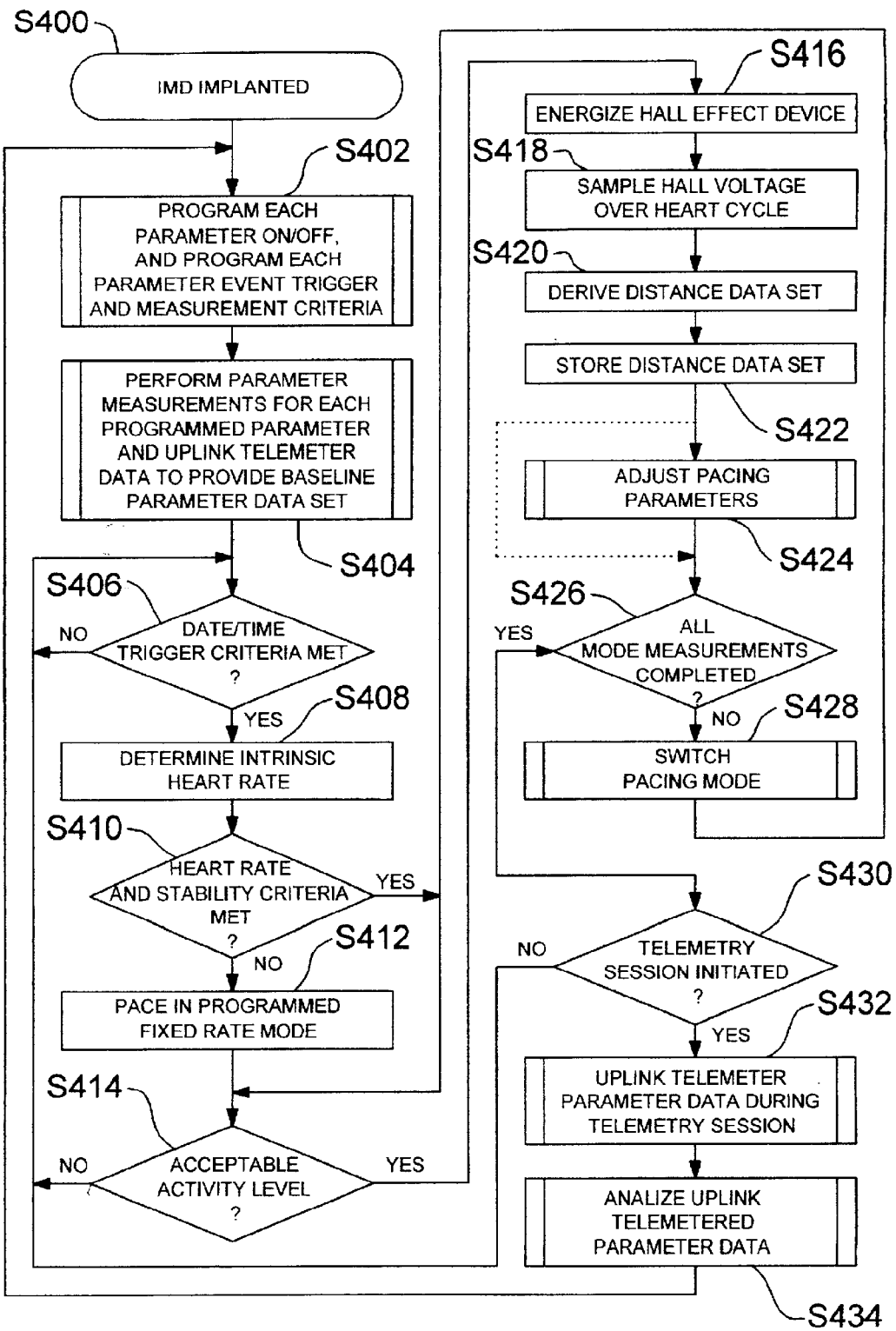
FIG. 6 is a flow chart illustrating the steps of periodically operating the system of FIG. 2 to derive distance signals and cardiac EGM signals, storing the signals, and telemetry transmitting the stored data and updated parameters to an external programmer.

Dimension Testing:

FIG. 6 illustrates the overall IMD function from the time of implantation (step S400) and initial programming (step 402) and baseline parameter measurements (step S404) through successive cycles of gathering parameter data in the IMD (steps S406–S422), optionally optimizing the pacing parameters in step S424, changing pacing mode, and repeating steps S414–S424, uplink telemetry transmission of the accumulated data to an external programmer (steps S430 and S432) for display and analysis (step S434), leading to possible reprogramming (step S402) and baseline parameter measurement (step S404) to better assess and provide pacing therapies for the heart failure state. The present invention may be implemented into a versatile multi-chamber pacing system as described above or into a less comprehensive pacing system offering fewer programmable pacing parameters and operating modes.

Each measured parameter may be programmed ON or OFF, and a particular event trigger for starting measurement of the programmed ON parameter as well as any specific measurement criteria can be programmed in step S402 using conventional downlink telemetry transmitted commands that are received in the telemetry transceiver 124 and forwarded to the microcomputer-based control and timing system 102. The physician may initially program the pacing system to deliver a pacing therapy in accordance with options provided in the flow charts of FIGS. 3 through 5B as described above. At a minimum, the pacing system of IMD 100 would be programmed to operate as a bi-ventricular pacing system or as an AV synchronous bi-ventricular pacing system.

In step S404, baseline parameter measurements are optionally performed for each programmed ON parameter to collect baseline or reference parameter data, to both store such data in IMD memory and to uplink telemetry transmit the parameter data for observation by the physician and for use in programming the operating modes and parameter values. The initial and updated baseline parameter measurements can be stored in the IMD RAM memory and/or stored externally in a patient file maintained by the physician with a date and time stamp and other pertinent data, e.g. patient activity level measured by activity signal processor circuit 118 and patient heart rate, if measurable.

After implant, the programmed ON parameters are measured in step S416 when an event trigger for the specific parameter occurs and when heart rate and/or rhythm criteria are met as set forth in steps S408–S414. The event criteria of step S406 may be a programmed time or multiple times of every day or specified days of the week or month as tracked by a date/time clock within the microcomputer-based timing and control system 102 or the detection of the patient initiated parameter measurement or some other programmed event, e.g., a combination of the time or times of day and a level of patient exercise indicated by the activity signal processor circuit 118.

Typically, the collection of the data in step S404 and step S416 should take place when the heart rate is in a normal range and is stable within a certain stability tolerance which can both be programmed by the physician and are determined over a series of heart cycles in steps S408"S412 in a manner well known in the art. The measurement of the data also only takes place in step S416 when the patient is at rest or within an acceptable level of exercise as determined in step S414. Typically, in step S408, incidences of spontaneous RA-EVENTs and RV-EVENTs would be monitored while the escape interval establishing the pacing rate is set to the lower rate interval (LRI) to determine the intrinsic heart rate.

The heart rate would be established at the pacing lower rate limit (LRL) or another programmed rate in step S412 if the intrinsic heart rate cannot be determined in this way or is unstable as determined in step S410. The atrial and ventricular pacing pulses will be delivered during the test if the patient's intrinsic heart rate is lower than the LRI established pacing rate, and consequently the heart rate will be inherently low and stable under these circumstances.

The measurement and storage of the dimension data is then conducted in steps S416–S422 over a programmed number of heart cycles or a time period if the activity criteria continues to be met in step S414. The heart rate and/or stability continues to be monitored through steps S416 and S418, and the pressure and dimension measurement that is commenced in step S416 may also be aborted if the heart rate and/or stability changes such that the heart rate/stability criteria become no longer satisfied in step S410 before the parameter measurement steps are completed.

The physician may program the IMD 100 to perform one or more of the dimension D1, D2, D3, D4 measurements over one or more heart cycles in a single session initiated in step S406. In one case, a single dimension data set can be obtained and stored in steps S416–S422 or multiple data sets can be obtained and the signals processed to derive average dimension values that are stored in steps S420 and S422.

If step S424 is programmed ON, the pacing parameters can be automatically optimized so as to maximize the detected mechanical movement of the heart, particularly the left ventricle, by performing the steps of FIG. 7, described further below.

The distance D1, D2, D3, D4 data sets can be obtained while the pacing system is operating in one of the above-described programmed pacing modes and then optionally repeated in other operating modes temporarily entered in step S428 depending upon a programmed-in command. A determination of whether all such programmed measurement modes are completed is made in step S426. The pacing mode is switched in step S428 to the next mode to repeat steps S414–S426 if all measurements made in all programmed modes are not yet completed. The completed distance data is stored in IMD memory with a date and time stamp and any other pertinent information, e.g., patient activity level, intrinsic heart rate, etc., in step S422. The history of the number, times and dates of successive parameter measurements can also be stored in IMD memory, but the stored parameter data and related data may be discarded on a FIFO basis if the memory capacity assigned to such data storage is exceeded.

It should be noted that the distance data sets that are derived over a heart cycle can be subjected to compression techniques so that only meaningful distance data is stored in memory registers. The primary distance data of interest is that taken during the portion of the heart cycle when the ventricles contract in systole generally corresponding to the PQRST waveform of the EGM and relax in asystole at the end of the T-wave.

Steps S406 through S426 are repeated each time that the event trigger criteria for the distance measurement are satisfied in step S406. The data collection continues until the accumulated data is uplink telemetry transmitted to the physician in steps S430 and S432. The physician then reviews the accumulated data in step S434 to determine if the dimension data reveals a trend. Dimension trend data can evidence changes in stroke volume (as derived from cardiac displacement), contractility (as derived from cardiac velocity), pre-ejection period (as derived from cardiac velocity) and ejection time (which is related to stroke volume), to optimize cardiac output. The data is gathered over a period of days, weeks and months provides a valuable indication as to whether the heart failure state is improving, worsening or staying about the same. The physician can then reprogram pacing operating modes and parameter values in steps S402 and S404 to provide a more efficacious therapy.

In S424, changes are automatically made to the SAV delay, PAV delay and/or V-V delay to derive a maximal change in distance $\Delta D_{MAX}$ as measured between any of the above-described distances from a series of measured $\Delta D_{SAMPLE}$ values obtained by dithering the values of one or more of the V-V delay, the SAV delay and the PAV delay. Step S424 can be programmed ON or OFF and thereby bypassed in FIG. 7. No parameter changes are made if step S424 is programmed OFF, but the physician still obtains valuable trend data in the course of following the steps of FIG. 6 that can be analyzed to determine whether the patient's heart failure state is improving or deteriorating. If it appears that the distance data is remaining stable, then it may be presumed that the applied pacing therapy and drug therapy is of benefit.

In one variation of this aspect of the invention, the SAV delay and/or PAV delay and/or V-V delay providing the $\Delta D_{MAX}$ is derived over N heart cycles wherein pacing is successively applied employing incremented or decremented ones of the SAV delay, PAV delay and/or V-V delay. The set of N derived $\Delta D_{SAMPLE}$ values derived at each adjusted delay are compared to determine the greatest attainable $\Delta D_{SAMPLE}$ value, that is, $\Delta D_{MAX}$. The currently prevailing SAV delay, PAV delay and/or V-V delay are then changed to the SAV delay, PAV delay and/or V-V delay that provides the maximum $\Delta D_{MAX}$ value.

Figure 7:
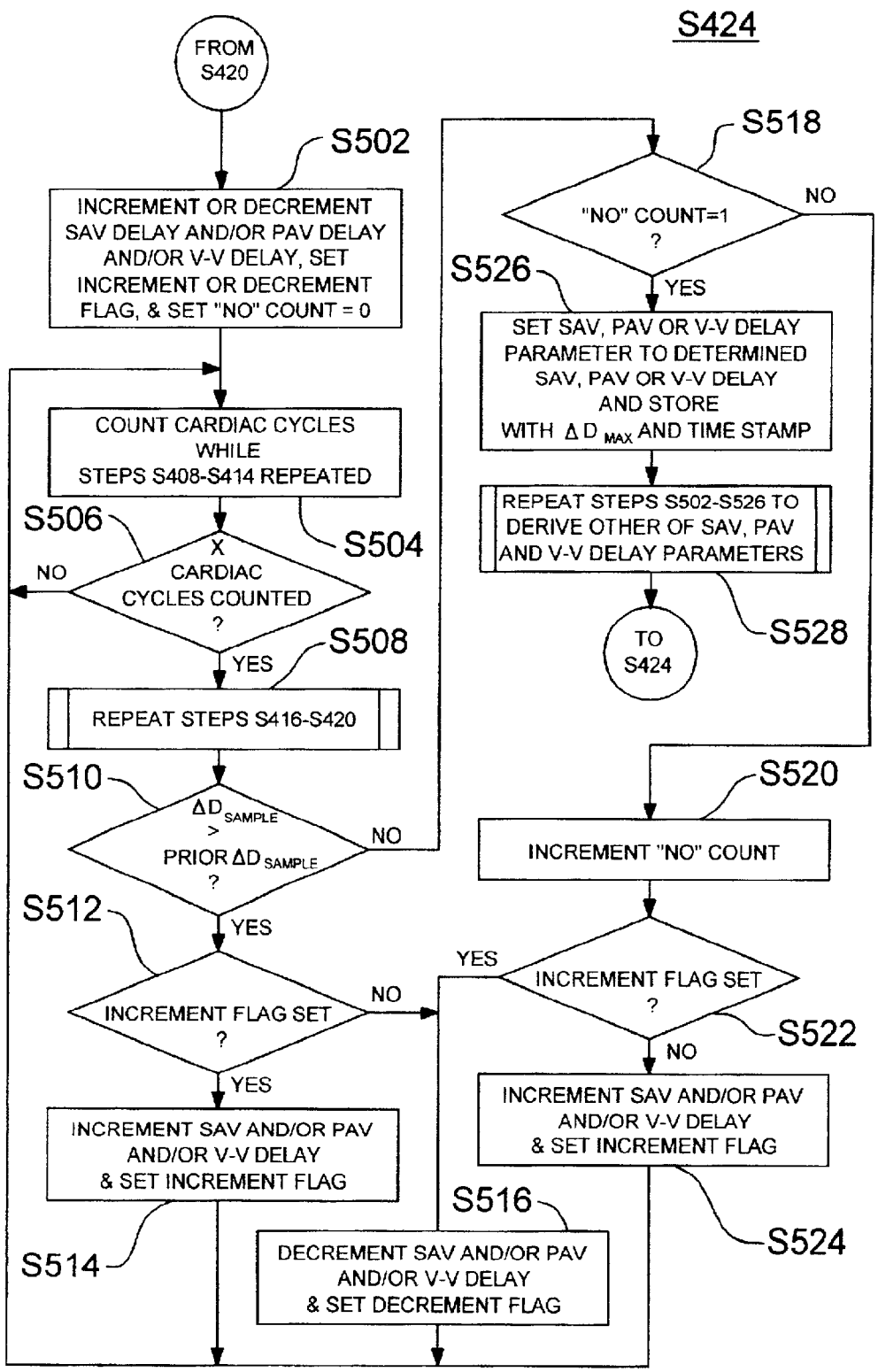
FIG. 7 is a flow chart illustrating the steps of operating the system of FIG. 2 to derive distance measurements pursuant to FIG. 6 and cardiac EGM signals and for processing the signals to update pacing timing parameters to optimize mechanical heart function.

One algorithm for determining the values of the SAV delay, PAV delay, and/or V-V delay that provide the $\Delta D_{MAX}$ following delivery of one of the V-PACE2 is Illustrated in FIG. 7. At this point, the first measured $\Delta D_{SAMPLE}$ value at the prevailing V-V delay, SAV delay and PAV delay has been stored in step S420. Each of a series of $\Delta D_{SAMPLE}$ values that are measured after a change in one or more of the V-V delay, SAV delay, and PAV delay are compared with the preceding or prior measured $\Delta D_{SAMPLE}$ value to determine if the incremental change causes an increase or decrease in the amount of contraction of the LV. An additional change in the same direction (increasing or decreasing the parameter duration) is made if the prior change does increase the rate of change of the distance D. But, the change direction is reversed to repeat the measurement of the $\Delta D_{SAMPLE}$ value using the prior parameter value, if the change results in an decrease in the measured $\Delta D_{SAMPLE}$ value. Only one reversal in direction is allowed to inhibit "hunting" that could otherwise occur and cause the algorithm to repeat the dithering indefinitely. A rest period of a number of heart cycles or a time period is provided between each change in a V-V delay, SAV delay, and PAV delay parameter value to allow the heart to acclimate to the change.

Thus, in step S502 one or more of the SAV delay and/or PAV delay and/or V-V delay are either incremented or decremented, the corresponding increment or decrement flag is set so that the direction of change (increase or decrease) is recorded, and a "NO" count is set to "0". Then, the resting period is timed or counted out in steps S504 and S506. It will be understood that a physician may establish an incrementing and decrementing routine from the patient work-up in steps S402 and S404 to determine which of the parameters and combinations of parameters effect a change in the $\Delta D_{SAMPLE}$ value in the particular patient. The physician can also program the increment and decrement amounts and the length of the resting period of steps S504 and S506. The physician can also program the system to abort or continue the process after a delay if steps S410 or S414 are not satisfied.

At this point, steps S416–S420 are repeated per step S508 to derive a succeeding measured $\Delta D_{SAMPLE}$ value at the decremented or incremented one or more of the V-V delay and/or SAV delay and/or PAV delay that is can be stored in memory in step S420 to retain a record of the operation of the algorithm for retrieval and review by the physician in a subsequently initiated telemetry session. The succeeding measured $\Delta D_{SAMPLE}$ value is compared to the prior measured $\Delta D_{SAMPLE}$ value in step S510. If the succeeding measured $\Delta D_{SAMPLE}$ value is greater than the prior measured $\Delta D_{SAMPLE}$ value, then the flag status is checked in step S512. If the increment flag was set in step S502, and the increment has effected the favorable increase in the $\Delta D_{SAMPLE}$, then the one or more of the SAV delay and/or PAV delay and/or V-V delay that was incremented in step S502 is again incremented in step S514. Similarly, if the decrement flag was set in step S502, and the decrement has effected the favorable increase in the $\Delta D_{SAMPLE}$, then the one or more of the SAV delay and/or PAV delay and/or V-V delay that was decremented in step S502 is again decremented in step S516. The process of steps S504–S516 is then repeated to determine if the $\Delta D_{SAMPLE}$ can be further increased.

Returning to step S510, if the succeeding measured $\Delta D_{SAMPLE}$ value is less than the prior measured $\Delta D_{SAMPLE}$ value, which can occur in first pass through steps S502 through S508 or in subsequent passes through S504–S516, then a change in direction is initiated. The "NO" count (set to "0" in step S502) is checked in step S518 and incremented to "1" in step S520. The flag status is checked in step S522 to determine the prevailing direction of change, and the change in direction is effected in step S516 or S524. Thus, if the one or more of the SAV delay and/or PAV delay and/or V-V delay was decremented previously, then the direction is changed in step S524 to increment the one or more of the SAV delay and/or PAV delay and/or V-V delay and to repeat steps S504–S510.

At some point, the succeeding measured $\Delta D_{SAMPLE}$ value is greater than the prior measured $\Delta D_{SAMPLE}$ value, whereupon the condition of step S518 is satisfied. Then, the prior measured $\Delta D_{SAMPLE}$ value is declared the $\Delta D_{MAX}$ value, and it and the corresponding one or more of the SAV delay and/or PAV delay and/or V-V delay are stored in RAM and employed in the operating system as described above with respect to FIGS. 4 through 6B until step S422 is repeated upon a trigger event satisfying step S406.

Alternatively, the incremented or decremented preceding value of the one or more of the SAV delay and/or PAV delay and/or V-V delay are stored in RAM and employed in the operating system as described above with respect to FIGS. 4 through 6B until step S422 is repeated upon a trigger event satisfying step S406 the first time the condition of step S510 is not satisfied.

The physician can also enter programming commands that enable successive changes in each of the SAV delay, PAV delay and V-V delay to be tested pursuant to steps S502-S526 and the above-described variants. Therefore, the next one of the synchronous pacing delays can be tested after a previous synchronous pacing delay has been derived by repeating steps S502–S526 pursuant to step S28 until all of the delay values have been derived. In many clinical cases, only the optimal V-V delay in the RV-LV or LV-RV sequence would be obtained. In other clinical cases, the optimal SAV delay would be first obtained, and then the optimal V-V delay in the RV-LV or LV-RV sequence would be obtained. In certain clinical cases, the PAV delay would be automatically set to be the same as the optimal SAV delay derived through steps S502–S526 various combinations. The order of the process and the tests included in the process can b left to the clinicians to develop for the particular patient.

The resulting values of the SAV delay, PAV delay and/or the V-V delay are stored with the corresponding $\Delta D_{MAX}$ data and the other related data in step S526 and employed in the operating system depicted in FIGS. 4 through 6B until the event criteria are next satisfied. Therefore, in this aspect, the present invention can be employed to selectively derive the SAV delay and/or PAV delay and/or the V-V delay that optimally maximizes the strength of contraction of the heart chamber.

Confirmation of Malignant Tachyarrhythmia:

Current ICDs and other anti-tachyarrhythmia control devices analyze the intrinsic atrial and/or ventricular heart rate, rate stability and/or EGM morphology to determine over a number of heart cycles whether a high intrinsic atrial or ventricular heart rate is sinus in nature, and not harmful, or malignant and requiring delivery of a burst stimulation or cardioversion/defibrillation shock therapy. Diminished shortening of either the RV-LV distance D1 during systole can be employed to verify a provisional determination of a malignant tachyarrhythmia in the ventricles. Alternately, if a ventricular arrhythmia is detected by analysis of the intrinsic atrial and ventricular heart rate, rate stability, and/or EGM morphology, the measurement of systolic shortening of either the RV-LV distance D1 and/or the RV-LA distance D2 can be used to gauge the urgency for terminating the arrhythmia. Arrhythmias with larger systolic shortening of D1 or D2 may be hemodynamically stable, thus allowing time for several burst stimulation attempts at termination. Arrhythmias with small systolic shortening of D1 or D2 may be hemodynamically unstable and should be treated immediately with cardioversion/defibrillation shock therapy.

Moreover, the strength of contractions of the arrhythmic heart chamber can be determined as a function of the measured distances, and the selection and delivery of either burst anti-tachycardia pacing or an electrical cardioversion/defibrillation shock can be made depending on the strength of contractions of the heart chamber.

Detection of Electromechanical Dissociation During Pacing or Arrhythmias:

At times, especially after delivery of an anti-tachyarrhythmia therapy to terminate a malignant tachyarrhythmia, the electrical activity of the atria and ventricles indicate slow heart rhythm yet the mechanical pumping action of the heart is absent or greatly impaired. Thus, the heart function is not fully restored although the termination of tachyarrhythmia is determined by the IMD from the normal sense event signals that do not satisfy tachyarrhythmia detection criteria that would, if satisfied, indicate failure of the anti-tachyarrhythmia therapy or resumption of the tachyarrhythmia. This condition, referred to as pulse less electrical activity (PEA), can be detected by normal electrical sensing of the IMD but diminished mechanical contraction as sensed by the measured distances D1–D3. In this situation, alternative forms of electrical stimulation of the myocardium may be beneficial.

Therefore, an appropriate one of the distance measurements D1, D2 and D3 are obtained over a time period following delivery of a cardioversion/defibrillation therapy to a heart chamber, to determine that the heart chamber is functioning mechanically. The efficacy of the delivered anti-tachyarrhythmia therapy can be determined and mistaken reliance on electrical activity in a PEA state can be avoided.

Mechanical Confirmation of Capture:

The thresholds for pacing stimuli are difficult to determine from electrical activity alone. Minimization of the energy of pacing stimuli is useful for increasing battery longevity, but if pacing stimuli are too small, patient safety is jeopardized. The method and apparatus of the present invention would provide proof of mechanical contraction of the heart in response to a pacing stimulus, thereby facilitating safe minimization of pacing energy.

In general, in FIGS. 1 and 2, a pacing pulse is delivered to any the RA, RV, LA and LV pace/sense electrode pairs to elicit a contraction of the respective heart chamber. The appropriate distance D measurement is obtained over the time following delivery of the pacing pulse to measure the distance changes that would occur if the pacing pulse captures the heart chamber and causes a contraction. If the measured distance data indicates that the pacing pulse energy captured the heart chamber, then, the pacing pulse energy of succeeding pacing pulses could be decremented to reduce pacing pulse energy. If a contraction is not indicated by the measured distance data, then an appropriate response would be instituted, e.g., incrementally increasing the pacing energy of succeeding delivered pacing pulses and repeating the above steps until the pulse energy is sufficient to elicit the contraction of the heart chamber upon delivery of each pacing pulse. A high energy back-up pacing pulse could also be delivered each time that the pacing pulse fails to capture the heart. Usually, the determination of the pacing threshold sufficient to capture the heart is done periodically, and pacing pulse energy is set to the determined threshold energy plus a safety margin energy increment and remains constant between periodic determinations of the capture threshold.

Chronic Monitoring of Contractility and Cardiac Output:

Cardiac output is perhaps the most important overall parameter of cardiac performance, but it is difficult to measure acutely, and has never been measured chronically in humans. The method and apparatus of the present invention would provide a chronic surrogate measurement of cardiac output, which could greatly enhance the patient's overall medical care. A relative measure of changes in cardiac output over time would be obtained by measuring the systolic shortening of the LV-RV distance D1, multiplied by the current heart rate. An absolute measure of cardiac output would require the physician to first establish the relationship between stroke volume and the systolic shortening of the LV-RV distance D1. The stroke volume measurement could be obtained for example by transthoracic ultrasound as is well known in the art.

A second important parameter of cardiac performance is the cardiac contractility. There is a strong correlation between the measured rate of systolic shortening of the LV-RV distance D1 and the maximum change in LV pressure during systole (dP/dT), an established measurement of cardiac contractility. Therefore, the measured rate of systolic shortening of the LV-RV distance D1 can serve as a surrogate measurement of cardiac contractility.

Rate Responsive Pacing:

Delivering a pacing therapy that includes physiological changes in heart rate is a longstanding problem. The method and apparatus of the present invention can measure cardiac contractility, which can be used to modulate heart rate.

In FIG. 2, the pacing rate determined by micro-computer-based timing and control system 102 can be programmed to develop a pacing rate from rate control parameters including the activity signal generated by activity signal processor circuit 118 and the determined cardiac contractility. The determination of the pacing rate can be dependent upon the determined contractility alone or in combination with the activity signal following a variety of algorithms well known in the art.

Automatic Adjustment of Sense Amplifier Sensitivity:

IMDs that sense the electrical activity of the heart usually include thresholds for separating electrical noise from cardiac events. These thresholds are often programmed by the physician after implant and during follow-up visits. The method and apparatus of the present invention could provide the necessary feedback for automated adjustment of sense amplifier sensitivity, by reporting mechanical contractions, which should be detected by the sense amplifier but were not accompanied by a sense event output by the sense amplifier.

In FIG. 2, the sense amplifiers in the input signal processing circuit 108 are adjustable in sensitivity by an appropriate timing and control signal to sense electrical activity across the RA, LA, RV and LV pace/sense electrode pairs in the pacing system so as to only sense signals of interest in that heart chamber and provide a sense event signal while avoiding oversensing of noise or electrical signals originating in the other heart chambers. The sensitivity of a sense amplifier associated with sensing cardiac depolarization signals of a heart chamber having a permanent magnet 80 that would move with a pace pulse elicited contraction or spontaneous contraction could be tested. The Hall effect device 70 is energized, and the distance D measurement from movement of the permanent magnet 80 during a contraction of the chamber is measured. If a contraction is evidenced by the measured distance data that is not accompanied by a sense event signal output by the sense amplifier, then a sense event signal may be declared and the sensitivity of the sense amplifier increased. Usually, the determination of the sensing threshold sufficient to accurately detect signals of interest and not sense other signals is done periodically, and the sensing threshold is set to the determined sensing threshold plus a sensitivity increment and remains constant between periodic determinations of the sensing threshold.

Detection of 2:1 Pacing:

As pacing rate increases, the heart often enters a state where every other paced beat does not result in mechanical contraction. This results in an instantaneous reduction of heart rate by 50%, and great discomfort to the patient. The method and apparatus of the present invention could be used to detect the absence of every other mechanical contraction that should follow delivery of each paced event and adjust pacing rate to a rate where 2:1 pacing no longer occurs.

In general, in FIGS. 1–3, a pacing pulse is delivered to any the RA, RV, LA and LV pace/sense electrode pairs to elicit a contraction of the respective heart chamber having a permanent magnet 80 that would move with a pace pulse elicited contraction. The Hall effect device 70 is energized, and the distance D measurement from movement of the permanent magnet 80 during a contraction of the chamber is measured. If a contraction is not indicated by the measured distance data, then an appropriate response would be instituted, e.g., the above-described stimulation threshold determination. If the increased pacing energy does not solve the loss of capture, if a 2:1 loss of capture pattern is evident, and if pacing rate is elevated above the lower rate limit, then the pacing rate of succeeding delivered pacing pulses can be decreased to a rate where the 2:1 pattern is no longer evident.

Appropriate Pacemaker Mode Switching:

Pacemakers are often programmed to deliver ventricular pacing synchronously with observed intrinsic atrial activity. This can cause hemodynamic instability when atrial arrhythmias develop. Modern pacemakers attempt to detect changes in atrial activity consistent with atrial arrhythmias, and automatically convert to a pacing mode in which ventricular activity does not track atrial activity. The method and apparatus of the present invention could directly detect the ventricular hemodynamic changes that call for a mode switch.

Monitoring Atrial Mechanical Function:

Because of the small muscle mass of the atria relative to the ventricles, atrial electrical activity is of much lower amplitude than ventricular electrical activity. The atrial electrical activity is often difficult to detect, and the neighboring ventricular electrical activity can often be mistakenly detected in the atrial electrogram, causing false sensing or oversensing. The method and apparatus of the present invention could be used to monitor atrial mechanical electrical activity, to detect the presence of arrhythmias or ineffective atrial contraction (i.e., contraction against a closed tricuspid or mitral valve), and to reject the erroneously sensed ventricular electrical activity.

In FIGS. 1 and 2, Hall effect device 70 is energized periodically over the heart cycle, and the distance D2 measurement is obtained between the Hall effect device 70 and permanent magnet $80_2$ on the LA lead 52 (or a permanent magnet 80 can be included in one of the RA on the RA lead 16). The mechanical contraction of the LA (or RA) is determined from the changes in the distance D2 and correlated to the output of the LA sense amplifier. If an atrial contraction is not indicated by the measured distance data, then the LA sense event signal is ignored, and LA sense amp sensitivity can be adjusted as described above to attempt to minimize oversensing. Conversely, it may be appropriate to declare an LA sense event from the distance measurement and eliminate reliance upon the LA sense amplifier.

Prediction of Syncope:

Early prediction of syncope could lead to the application of preventative therapy. Reduction of cardiac output or other changes in mechanical activity or size of the heart may precede syncope and could be used to time the delivery of preventative therapy.

SUMMARY

All patents and publications referenced herein are hereby incorporated by reference in there entireties.

It will be understood that certain of the above-described structures, functions and operations of the pacing systems of the preferred embodiments are not necessary to practice the present invention and are included in the description simply for completeness of an exemplary embodiment or embodiments. It will also be understood that there may be other structures, functions and operations ancillary to the typical operation of an AV synchronous, three or four chamber pacemaker that are not disclosed and are not necessary to the practice of the present invention. In addition, it will be understood that specifically described structures, functions and operations set forth in the above-incorporated patents and publications can be practiced in conjunction with the present invention, but they are not essential to its practice. It is therefore to be understood, that within the scope of the appended claims, the invention may be practiced otherwise than as specifically described without actually departing from the spirit and scope of the present invention.

What is claimed is:

1. A method for monitoring patient cardiac signals and the contraction and expansion of the heart chambers during heart cycles and processing such signals within an implantable medical device (IMD) to provide data related to the mechanical performance of the heart comprising:

implanting a magnetic field strength sensor at a sensor site in or on a first heart chamber;

implanting a megnatic field generator that generates a magnetic field at a magnet site in or on a second heart chamber displaced from the sensor site at a distance that fluctuates with the contraction and expansion of at least the first heart chamber; and operating the magnetic field strength sensor during at least a portion of the heart cycle to develop a sensor output signal having a magnitude and rate of field directly related to the distance between the magnet and sensor sites that fluctuates with the contraction and expansion of one or both of the first heart chamber and second heart chamber, whereby the output signal magnitude or rate of change of magnitude is representative of the mechanical performance of the heart chamber, wherein the implantable medical device comprises an implantable pacing system, and further comprising:

delivering first and second pacing pulses separated in time by a pace delay to the first and second heart chambers, respectively, wherein the first and second heart chambers are right and left heart chambers, to elicit synchronized contractions of the first and second heart chambers;

conducting the operating step after delivery of the pacing pulse; and adjusting the timing of delivery of the first and second pacing pulses as a function of the determined distance during a heart cycle following delivery of first and second pacing pulses to maximize the value of a weighted combination of the systolic shortening of the distance and the inverse of the end diastolic distance for a given heart rate.

2. A method for monitoring patient cardiac signals and the contraction and expansion of the heart chambers during heart cycles and processing such signal within an implantable medical device (IMD) to provide data related to the mechanical performance of the heart comprising:

implanting a magnetic field strength sensor at a sensor site in or on a first heart chamber;

implanting a magnetic field generator that generates a magnetic field at a magnet site in or on a second heart chamber displaced from the sensor site at a distance that fluctuates with the contraction and expansion of at least the first heart chamber; and operating the magnetic field strength sensor during at least a portion of the heart cycle to develop a sensor output signal having a magnitude and rate of change in magnitude dependent upon the magnetic field strength of the magnetic field directly related to the distance between the magnet and sensor sites that fluctuates with the contraction and expansion of one or both of the first heart chamber and second heart chamber, whereby the output signal magnitude or rate of change of magnitude is representative of the mechanical performance of the heart chamber, wherein the implantable medical device comprises an implantable pacing system, and further comprising:

delivering a first pacing pulse to the left ventricle (LV) and a second pacing pulse to the right ventricle (RV) separated in time by a V-V pace delay to elicit synchronized contractions of the right and left ventricles;

conducting the operating step after delivery of the pacing pulse; and adjusting the V-V pace delay as a function of the determined distance between to maximize the value of a weighted combination of the systolic shortening of the RV-LV distance and the inverse of the and diastolic distance for a given heart rate.

3. A method for monitoring patient cardiac signals and the contraction and expansion of the heart chambers during heart cycles and processing such signals within an implantable medical device (IMD) to provide data related to the mechanical performance of the heart comprising;

implanting a magnetic field strength sensor at a sensor site in or on a first heart chamber;

implanting a magnetic field generator that generates a magnetic field at a magnet site in or on a second heart chamber displaced from the sensor site at a distance that fluctuates with the contraction and expansion of at least the first heart chamber; and operating the magnetic field strength sensor during at least a portion of the heart cycle to develop a sensor output signal having a magnitude and rate of change in magnitude dependent upon the magnetic field strength of the magnetic field directly related to the distance between the magnet and sensor sites that fluctuates with the contraction and expansion of one or both of the first heart chamber and second heart chamber, whereby the output signal magnitude or rate of change of magnitude is representative of the mechanical performance of the heart chamber, wherein the implantable medical device comprises an implantable pacing system, and further comprising:

delivering a first pacing pulse to the atria and a second pacing pulse to the ventricles to at least one of the right ventricle (RV) and the left ventricle (LV) separated in time by an AV delay to elicit synchronized contractions of the atria and ventricles;

conducting the operating step after delivery of the pacing pulse; and adjusting the AV delay as a function of the determined distance to maximize the value of a weighted combination of the systolic shortening of the RV-LV distance and the inverse of the end diastolic distance fore given heart rate.

4. A system for monitoring patent cardiac signals and the contraction and expansion of the heart chambers during heart cycles and processing such signals within an implantable medical device (IMD) to provide data related to the mechanical performance of the heart comprising:

a magnetic field strength sensor located at a sensor site in or aria first heart chamber;

a magnetic field generator that generates a magnetic field located at a magnet site in or on a second heart chamber displaced from the sensor site at a distance that fluctuates with the contraction and expansion of the heart chamber; and means for operating the magnetic field strength sensor during at least a portion of the heart cycle to develop a sensor output signal having a magnitude and rate of change of magnitude dependent upon the magnetic field strength of the magnetic field directly related to the distance between the magnet and sensor sites that fluctuates with the contraction and expansion of the heart chambers, whereby the output signal magnitude or rate in change of magnitude is representative of the mechanical performance of the heart chambers, wherein the implantable medical device comprises an implantable pacing system, and further comprising:

means for delivering first and second pacing pulses separated in time by a pace delay to the first and second heart chambers, respectively, wherein the first and second heart chambers are right and left heart chambers, to elicit synchronized contractions of the first and second heart chambers; and means for adjusting the timing of delivery of the first and second pacing pulses as a function of the determined distance during a heart cycle following delivery of first and second pacing pulses to maximize the value of a weighted combination of the systolic shortening of the distance and the inverse of the end diastolic distance for a given heart rate.

5. A system for monitoring patient cardiac signals and the contraction and expansion of the heart chambers during heart cycles and processing such signals within an implantable medical device (IMD) to provided data related to the mechanical performance of the heart comprising:

a magnetic field strength sensor located at a sensor site in or on a first heart chamber;

a magnetic field generator that generates a magnetic field located at a magnet site in or on a second heart chamber displaced from the sensor site at a distance that fluctuates with the contraction and expansion of the heart chamber; and means for operating the magnetic field strength sensor during at least a portion of the heart cycle to develop a sensor output signal having a magnitude and rate of change of magnitude dependent upon the magnetic field strength of the magnetic field directly related to the distance between the magnet and sensor sites that fluctuates with the contraction and expansion of the heart chambers, whereby the output signal magnitude or rate in chance of magnitude is representative of the mechanical performance of the heart chambers, wherein the implantable medical device comprises an implantable pacing system, and further comprising:

means for delivering a first pacing pulse to the left ventricle (LV) and a second pacing pulse to the right ventricle (RV) separated in time by a V-V pace delay to elicit synchronized contractions of the right and left ventricles; and means for adjusting the V-V pace delay as a function of the determined distance between to maximize the value of a weighted combination of the systolic shortening of the RV-LV distance and the inverse of the end diastolic distance for a given heart rate.

6. A system for monitoring patient cardiac signals and the contraction and expansion of the heart chambers during heart cycles and processing such signals within an implantable medical device (IMD) to provide data related to the mechanical performance of the heart comprising:

a magnetic field strength sensor located at a sensor site in or on a first heart chamber;

a magnetic field generator that generates a magnetic field located at a magnet site in or on a second heart chamber displaced from the sensor site at a distance that fluctuates with the contraction and expansion of the heart chamber; and means for operating the magnetic field strength sensor during at least a portion of the heart cycle to develop a sensor output signal having a magnitude and rate of change of magnitude dependent upon the magnetic field strength of the magnetic field directly related to the distance between the magnet and sensor sites that fluctuates with the contraction and expansion of the heart chambers, where the output signal magnitude or rate in change of magnitude is representative of the mechanical performance of the heart chambers, wherein the implantable medical device comprises an implantable pacing system, and further comprising:

means for delivering a first pacing pulse to the atria and a second pacing pulse to the ventricles to at least one of the right ventricle (RV) and the left ventricle (LV) separated in time by an AV delay to elicit synchronized contractions of the atria and ventricles; and means for adjusting the AV delay as a function of the determined distance to maximize the value of a weighted combination of the systolic shortening of the RV-LV distance and the inverse of the end diastolic distance for a given heart rate.

7. In a multi-site, cardiac pacing system having memory for storing data and wherein ventricular pacing pulses are delivered to first and second ventricular sites synchronously within a V-V pace delay at a predetermined pacing rate in accordance with the steps of:

implanting ventricular pace/sense electrodes at the first and second ventricular sites;

timing a ventricular pacing escape interval;

detecting a ventricular depolarization at a selected one of the first and second ventricular sites within the pacing escape interval and, in response, terminating the pacing escape interval and providing a first ventricular sense (VS) event;

delivering a first ventricular pace (VP) pulse to the selected one of the first and second ventricular sites upon either the time-out of the pacing escape interval without provision of a first VS event or upon provision of the first VS event during time-out of the pacing escape interval;

timing the V-V pace delay from a first VS event occurring prior to the time-out of the pacing escape interval or from a first VP pulse delivered either upon provision of the first VS event or upon time-out of the pacing escape interval; and delivering a second VP pulse to the other of the first and second ventricular sites upon the time-out of the V-V pace delay, whereby VP pulses are delivered to the first ventricular site and to the second ventricular sites at a V-V pace delay selected to enhance ventricular mechanical performance;

a method of periodically deriving trend data representative of the state of heart failure as evidenced by ventricular mechanical performance during the delivery of the VP pulses comprising the steps of:

implanting a magnetic field strength sensor at a sensor site in relation to the first ventricular site;

implanting a magnetic field generator that generates a magnetic field at a magnet site in relation to the second ventricular site and displaced from the sensor site at a distance that fluctuates with the contraction and expansion of the ventricles;

operating the magnetic field strength sensitive means during at least a portion of the heart cycle to develop a sensor output signal having a magnitude dependent upon the magnetic field strength of the magnetic field directly related to the distance between the magnet and sensor sites that fluctuates with the contraction and expansion of the ventricles, whereby the output signal magnitude is representative of the mechanical performance of the heart chambers; and storing the sensor output signal in memory, whereby trend data representative of the state of heart failure as evidenced by changes in the stored one of the elapsed VS-VS conduction time, the VP-VS conduction time, and the VS/VP-VS conduction time between the first and second ventricular sites is accumulated for analysis of the trend.

* * * * *

UNITED STATES PATENT AND TRADEMARK OFFICE
CERTIFICATE OF CORRECTION

PATENT NO.         : 6,959,214 B2                                          Page 1 of 1
APPLICATION NO.    : 09/996138
DATED              : October 25, 2005
INVENTOR(S)        : Forrest C.M. Pape et al.

It is certified that error appears in the above-identified patent and that said Letters Patent is hereby corrected as shown below:

Column 34, lines 58 and 59, delete "in or aria first" and insert --in or on a first--

Column 35, line 44, delete "or rate in chance" and insert --or rate in change--

Column 36, line 3, delete "chamber; and" and insert --chambers; and--

Column 36, line 11, delete "where the" and insert --whereby the--

Signed and Sealed this

Second Day of January, 2007

JON W. DUDAS
*Director of the United States Patent and Trademark Office*